(12) United States Patent
Evans et al.

(10) Patent No.: US 6,652,548 B2
(45) Date of Patent: Nov. 25, 2003

(54) EXPANSIBLE SHEARING CATHETERS FOR THROMBUS REMOVAL

(75) Inventors: Michael A. Evans, Palo Alto, CA (US); Denise M. Demarais, San Jose, CA (US); Stephen A. Leeflang, Stanford, CA (US); Christian S. Eversull, Palo Alto, CA (US)

(73) Assignee: Bacchus Vascular Inc., Santa Clara, CA (US)

( * ) Notice: Subject to any disclaimer, the term of this patent is extended or adjusted under 35 U.S.C. 154(b) by 74 days.

(21) Appl. No.: 09/823,652

(22) Filed: Mar. 30, 2001

(65) Prior Publication Data

US 2002/0010487 A1 Jan. 24, 2002

Related U.S. Application Data

(63) Continuation-in-part of application No. 09/820,301, filed on Mar. 27, 2001.
(60) Provisional application No. 60/260,170, filed on Jan. 4, 2001, and provisional application No. 60/193,539, filed on Mar. 31, 2000.

(51) Int. Cl.[7] .................................................. A61D 1/02
(52) U.S. Cl. ........................................................ 606/159
(58) Field of Search ................................. 606/159, 170, 606/180, 181, 190, 191, 194, 195, 198, 108, 200; 623/1.11, 1.12, 1.13, 1.14, 1.15, 1.16, 1.17, 1.18, 1.19, 1.2; 430/311, 312–320

(56) References Cited

U.S. PATENT DOCUMENTS

| | | |
|---|---|---|
| 3,320,957 A | 5/1967 | Sokolik |
| 4,631,052 A | 12/1986 | Kensey |
| 4,857,045 A | 8/1989 | Rydell |
| 4,886,061 A | 12/1989 | Fischell et al. |
| 5,085,662 A | 2/1992 | Willard |
| 5,176,693 A | 1/1993 | Pannek, Jr. |
| 5,178,625 A | 1/1993 | Groshong |
| 5,224,945 A | 7/1993 | Pannek, Jr. |
| 5,282,484 A | 2/1994 | Reger |
| 5,318,576 A | 6/1994 | Plassche, Jr. et al. |
| 5,462,529 A | 10/1995 | Simpson et al. |
| 5,490,859 A | 2/1996 | Misch et al. |
| 5,501,694 A | 3/1996 | Ressemann et al. |
| 5,527,326 A | 6/1996 | Hermann et al. |
| 5,540,707 A | 7/1996 | Ressemann et al. |
| 5,569,277 A | * 10/1996 | Evans et al. ................. 606/159 |
| 5,571,122 A | 11/1996 | Kelly et al. |
| 5,665,098 A | 9/1997 | Kelly et al. |
| 5,681,336 A | 10/1997 | Clement et al. |
| 5,725,549 A | * 3/1998 | Lam .......................... 623/1.15 |
| 5,766,191 A | 6/1998 | Trerotola et al. |
| 5,836,868 A | 11/1998 | Ressemann et al. |
| 5,879,361 A | 3/1999 | Nash |
| 5,885,258 A | 3/1999 | Sachdeva et al. |
| 5,904,698 A | 5/1999 | Thomas et al. |
| 6,027,514 A | 2/2000 | Stine et al. |
| 6,027,863 A | 2/2000 | Donadio, III |
| 6,036,708 A | 3/2000 | Sciver |

FOREIGN PATENT DOCUMENTS

| | | |
|---|---|---|
| EP | 0268228 | 1/1996 |
| WO | WO 98/34673 | 8/1998 |
| WO | WO 99/30624 | 6/1999 |

* cited by examiner

*Primary Examiner*—Kevin T. Truong
*Assistant Examiner*—Vy Q. Bui
(74) *Attorney, Agent, or Firm*—Townsend & Townsend & Crew LLP; Mark D. Barrish, Esq.

(57) ABSTRACT

Devices, methods, kits, and methods remove clot material from the vasculature and other body lumens. Expansible baskets may be used as cooperating radially expansible shearing members. Helically oriented struts of each basket may wind in a uniform circumferential direction. The struts can be independently flexible, allowing the shearing members to flex axially together. The inner basket may be rotatably driven and may use an axial pump extending proximally from the shearing members and/or a distal penetrator for advancing into an occlusion which inhibits guidewire access. The struts may slide substantially continuously across each other, and may be sufficiently aggressive for highly effective thrombectomy.

18 Claims, 20 Drawing Sheets

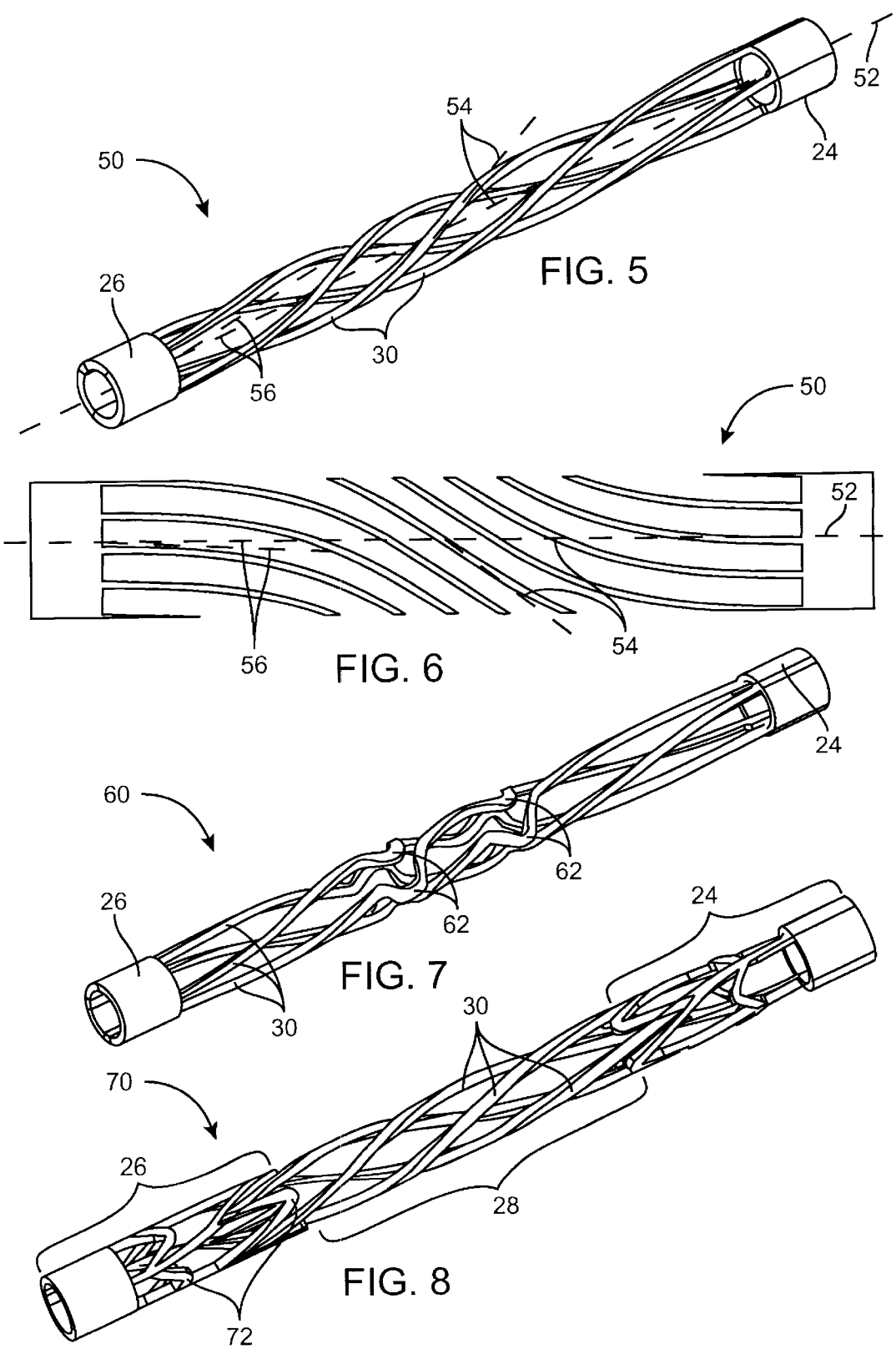

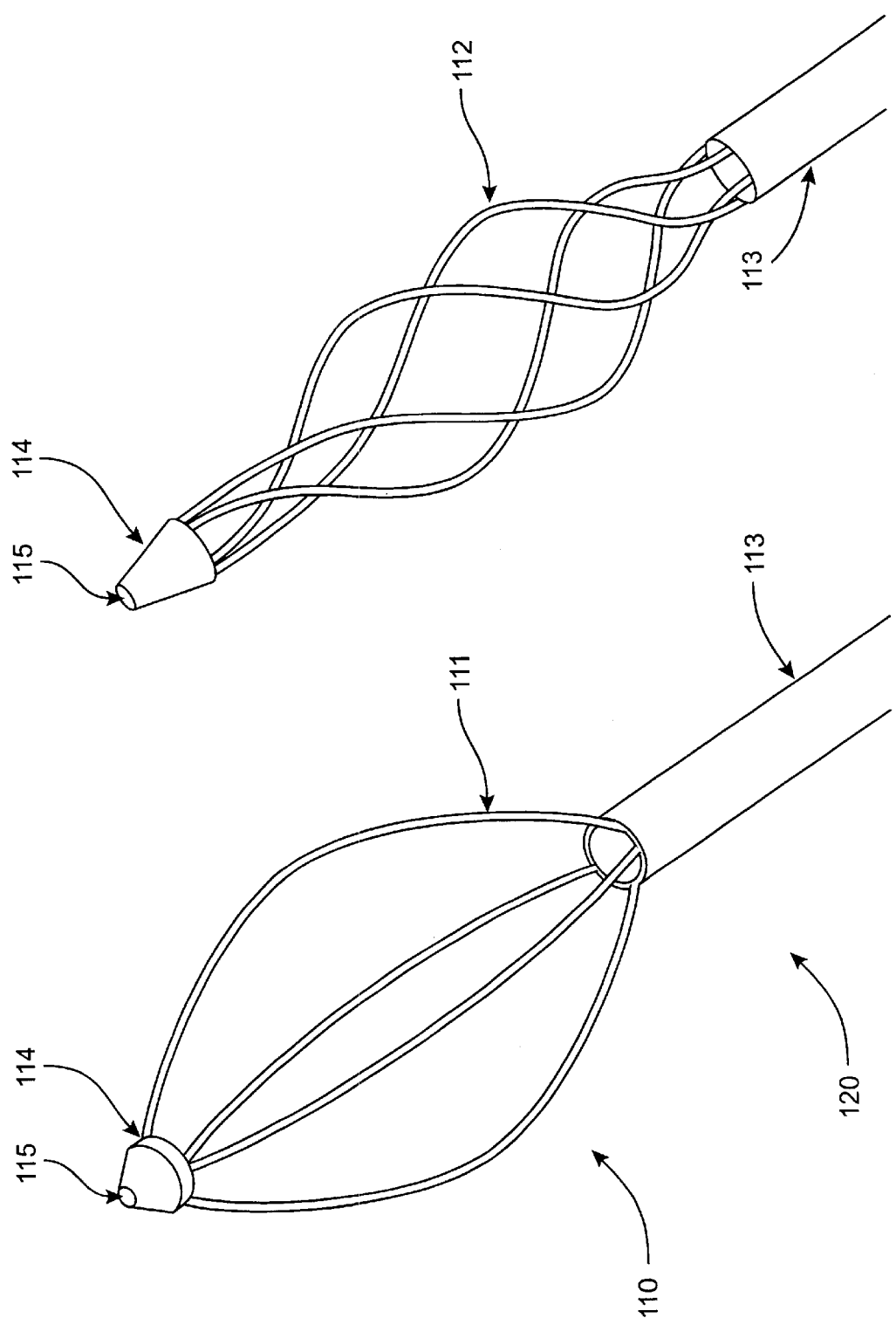

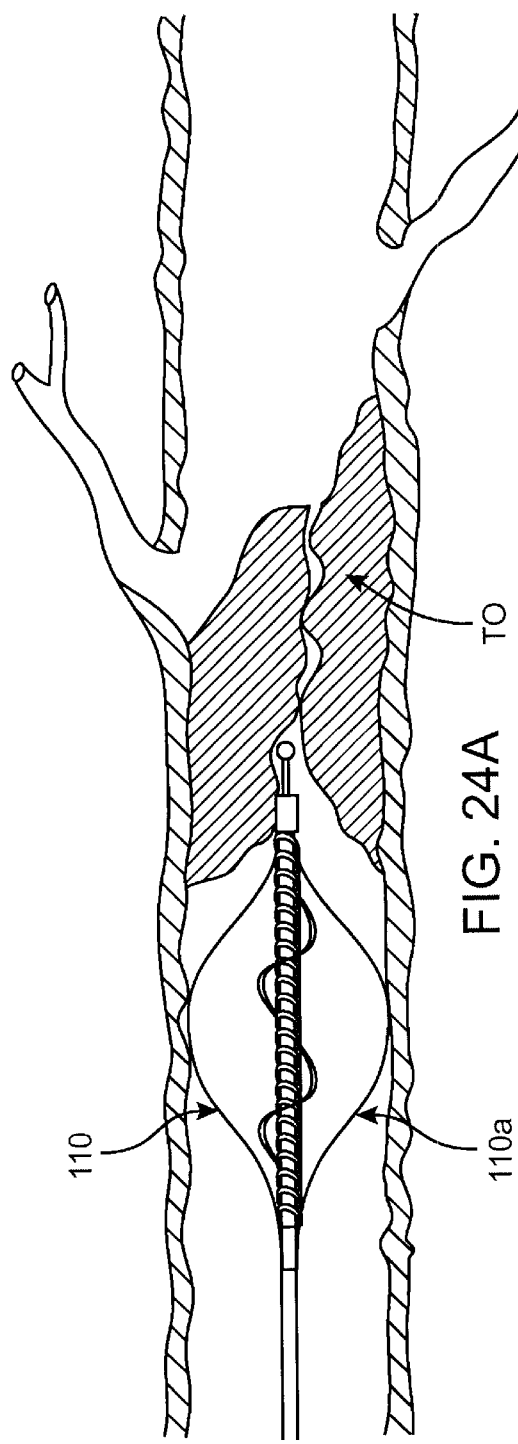
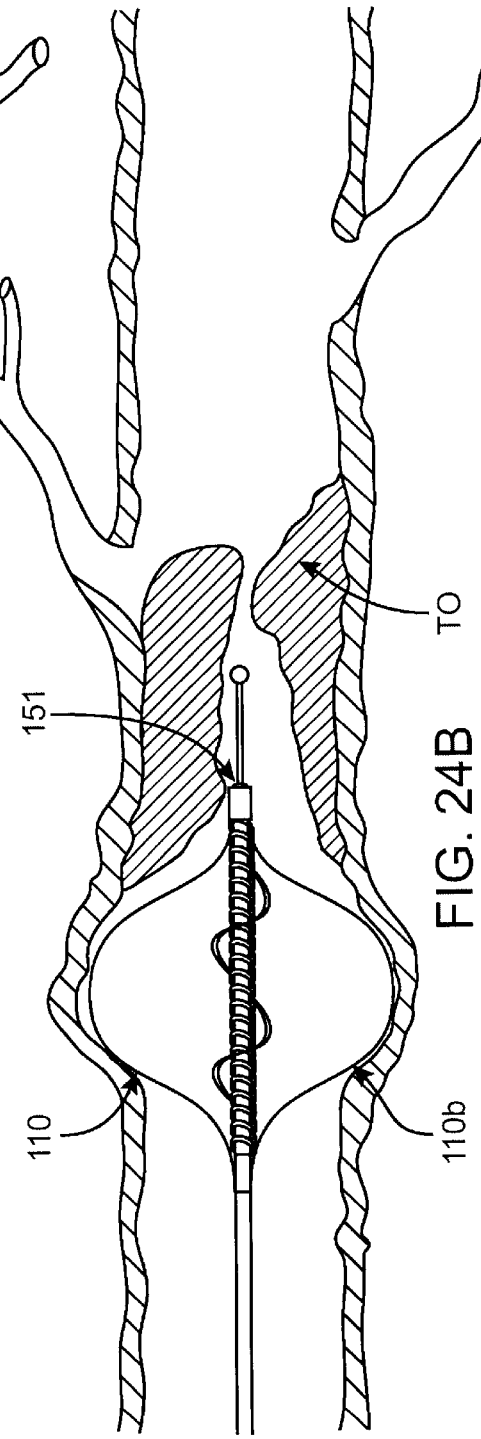

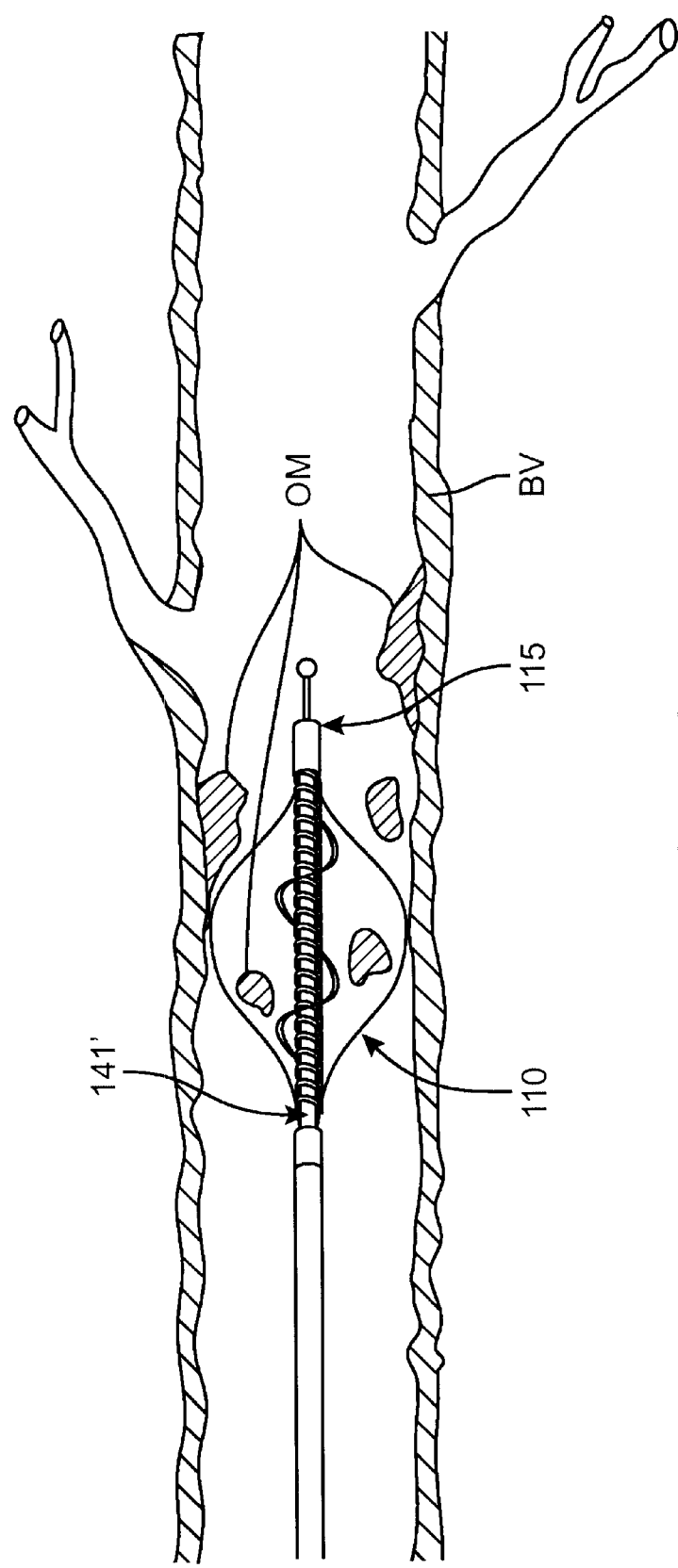

EXPANSIBLE SHEARING CATHETERS FOR THROMBUS REMOVAL

CROSS-REFERENCES TO RELATED APPLICATIONS

The present application claims the benefit of priority from Provisional Application No. 60/193,539 filed Mar. 31, 2000, and from Provisional Application No. 60/260,170 filed Jan. 4, 2001, and is a continuation-in-part application of application Ser. No. 09/820,301, filed on Mar. 27, 2001, the full disclosures of which are incorporated herein by reference.

BACKGROUND OF THE INVENTION

1. Field of the Invention

The present invention relates generally to medical devices and methods. In one embodiment, the present invention relates to devices and methods for disrupting, collecting, and removing thrombus from blood vessels and other body lumens.

Thrombosis and atherosclerosis are common ailments which occur in humans and which result from the deposition of thrombus and clot on the walls of blood vessels. When hardened, such deposits are commonly referred to as plaque. Such deposits are most common in the peripheral blood vessels that feed the limbs of the human body and the coronary arteries which feed the heart. Stasis, incompetent valves, and trauma in the venous circulation cause thrombosis, particularly occurring as a deep vein thrombosis in the peripheral vasculature. When such deposits build-up in localized regions of the blood vessel, they can restrict blood flow and cause a serious health risk.

In addition to forming in the natural vasculature, thrombosis is a serious problem in "artificial" blood vessels, particularly in peripheral femoral-popliteal and coronary bypass grafts and dialysis access grafts and fistulas. The creation of such artificial blood vessels generally involves anastomotic attachment at at least one, and usually at at least two, locations in the vasculature. Such sites of an anastomotic attachment are particularly susceptible to thrombus formation due to narrowing caused by intimal hyperplasia, and thrombus formation at these sites is a frequent cause of failure of the implanted graft or fistula. The arteriovenous grafts and fistulas which are used for dialysis access are significantly compromised by thrombosis at the sites of anastomotic attachment and elsewhere. Thrombosis often occurs to such an extent that the graft needs to be replaced within a few years or, in the worst cases, a few months.

A variety of methods have been developed for treating thrombosis and atherosclerosis in the coronary and peripheral vasculature as well as in implanted grafts and fistulas. Such techniques include surgical procedures, such as coronary artery bypass grafting, and minimally invasive procedures, such as angioplasty, atherectomy, transmyocardial revasculaturization, and the like. In many of the surgical clinical approaches to removing unwanted material, the treatment site is accessed directly through a surgical incision. Of particular interest of the present invention, a variety of techniques generally described as "thrombectomy" have been developed. Thrombectomy generally refers to procedures for the removal of relatively soft thrombus and clot from the vasculature. Removal is usually achieved by mechanically disrupting the clot, optionally with the introduction of thrombolytic agents. The disrupted thrombus or clot is then withdrawn through a catheter, typically with a vacuum or mechanical transport device.

Thrombectomy generally differs from angioplasty and atherectomy in the type of occlusive material which is being treated and in the desire to avoid damage to the blood vessel wall. The material removed in most thrombectomy procedures is relatively soft, such as the clot formed in deep vein thrombosis, and is usually not hardened plaque of the type treated by angioplasty in the coronary vasculature. Moreover, it is usually an objective of thrombectomy procedures to have minimum or no deleterious interaction with the blood vessel wall. Ideally, the clot will be disrupted and pulled away from the blood vessel wall with no harmful effect on the wall itself.

While successful thrombectomy procedures have been achieved, most have required comprise between complete removal of the thrombosis and minimum injury to the blood vessel wall. While more aggressive thrombectomy procedures employing rotating blades can be very effective at thrombus removal, they can present a significant risk of injury to the blood vessel wall. Alternatively, those which rely primarily on vacuum extraction together with minimum disruption of the thrombus, often fail to achieve sufficient thrombus removal.

In work related to the present invention, an expansible macerator for safely breaking up or disrupting thrombus and other occlusive materials has been proposed. U.S. patent application Ser. No. 09/454,517 filed on Dec. 6, 1999 and entitled "Systems and Methods for Clot Disruption and Retrieval," describes a catheter having an expansible positioning cage and a helical macerator positioned within the cage. The macerator can be separated from the surrounding cage so as to maintain separation between the macerator and a surrounding wall of the body lumen. This caged macerator represents a significant advancement in the art, as it allows disruption of soft clot while inhibiting trauma to blood vessels of varying diameters. However, as with all advances, still further improvements would be desirable. In particular, it may be beneficial to provide more aggressive and more rapid removal of clot material. It would also be helpful to allow the physician to selectively and controllably remove plaque or other more solid occlusive material during a thrombectomy, preferably using the thrombectomy catheter. It may also be beneficial to more uniformly urge the severed debris toward an aspiration port of the thrombectomy catheter.

In light of the above, it would be beneficial to provide improved devices, systems, methods, methods for manufacture, and kits for removing thrombus material from the vasculature and other body lumens. It would be particularly desirable to provide improved techniques for advancing a guidewire or guide catheter, positioning a treatment catheter across the blocking occlusion, isolating the treatment site, and further treating the occlusion while minimizing or eliminating any distal emboli. An improved procedure would also benefit from having a device that can rapidly aspirate the occlusive material from the body lumen. Optionally, these improved devices and methods might be used to treat a total occlusion as the treatment device is being advanced through the occlusion, facilitating placement of a wire across the occlusion so that further treatment can be easily commenced. Device and methods which allow creation of a channel through a total occlusion for placement of a guidewire would also be advantageous, as would improved debulking of stenotic tissues.

Some or all of these objectives may be met by the device and methods of the present invention.

2. Description of the Background Art

As mentioned above, systems and methods for clot disruption and removal related to the present invention are described in U.S. patent application Ser. No. 09/454,517. A related mechanical pump for removal of fragmented matter and methods was described in U.S. patent application Ser. No. 09/590915, filed on Jun. 9, 2000. A further related method and system for reinfusing filtered body aspirates is described in U.S. Provisional Patent No. 60/174,108, filed on Dec. 31, 1999.

A cutting stent with a flexible tissue extractor is described in U.S. Pat. No. 6,036,708. A compressible/expandable atherectomy cutter is described in U.S. Pat. No. 5,224,945. Unitary removal of plaque is described in U.S. Pat. No. 5,665,098. A method for performing a partial atherectomy is described in U.S. Pat. No. 5,282,484, while an atherectomy device having a helical blade and a blade guide is described in U.S. Pat. No. 5,569,277. A catheter arthrotome is described in U.S. Pat. No. 5,178,625. A surgical apparatus for transurethral resection is described in U.S. Pat. No. 3,320,957. A vessel deposit sharing apparatus is described in U.S. Pat. No. 5,527,326.

A coiled stent with locking ends is described in U.S. Pat. No. 5,725,549. A medical instrument with a slotted memory metal tube is described in U.S. Pat. No. 5,885,258. A method for manufacturing a tubular medical device is described in U.S. Pat. No. 6,027,863. The following U.S. Patent Nos. may also be relevant: U.S. Pat. Nos. 6,010,449; 5,968,064; 5,741,270; 5,766,191; 5,569,275; 5,501,694; 5,795,322; 5,904,968; 5,224,945; 5,312,425; 5,330,484; and 6,022,336.

All of the above references, and any and all other references cited in this application, are incorporated herein by reference in their entirety for all purposes.

SUMMARY OF THE INVENTION

The present invention provides improved devices, methods, kits, methods for fabrication, and the like, for removing thrombus from the vasculature. The invention generally makes use of cooperating radially expansible shearing members, each shearing members often being in the form of an expansible basket. The exemplary baskets comprise helically oriented struts, with the struts of each shearing member extending with a uniform circumferential direction. The struts will often be independently flexible between proximal and distal portions of the shearing members, which can allow the shearing the members to flex axially to follow axially curving body lumens. The inner basket may be rotatably driven within the outer basket, and may optionally be coupled to an axial pump extending proximally from the shearing members. The outer basket may be coupled to a catheter body to avoid excessive tissue trauma to the body lumen, and the helical struts of the shearing members can by helically counterwound, so that the inner struts may slide substantially continuously across the outer struts. The inner and outer baskets may both radially expand selectively, independently and/or with a single actuator. The resulting shearing action is sufficiently aggressive for highly effective thrombectomy, while use of a rotationally static and axially flexible outer basket may provide a safe, limited, and controllable treatment.

In a first aspect, the invention provides a thrombectomy catheter comprising a flexible tubular body having a proximal end and a distal end. An outer shearing member is attached near the distal end, the outer member having a perforate inner surface. An inner shearing member is rotatably disposed within the outer member, the inner member having a proximal portion, a distal portion, and a circumferential series of struts extending therebetween. The struts can flex to slide across the inner surface of the outer shearing member when the inner shearing member rotates.

Optionally, the inner member may rotate about an axis, and the inner and outer shearing bodies may be sufficiently flexible to deflect the axis laterally when the outer shearing member is expanded to engage a surrounding vessel and the inner member rotates therein. The struts may uniformly coil helically in a first circumferential orientation so that rotation of the inner shearing member toward the first circumferential orientation consistently urges sheared occlusive material proximally. The inner shearing member may comprise tube material, the struts being separated by cut surfaces between adjacent tube material portions. The outer shearing member may comprise outer tube material having a proximal outer portion, a distal outer portion and a circumferential series of outer struts extending helically therebetween, with the struts being separated by cut outer surfaces between outer adjacent tube material portions. The struts may be affixed together at the proximal portion and at the distal portion, and may flex independently therebetween.

The struts may be helically oriented with a local pitch of the struts varying axially along the struts. The local pitch can increase toward the proximal and distal portions sufficiently to inhibit excessive separation between adjacent struts when the outer shearing member flexes axially. The struts may have protrusions which inhibit sliding of thrombus axially between cooperating edges of the inner and outer shearing bodies. At least one expansion actuator may extend proximally from the shearing members so that the inner and outer shearing members can be radially expanded in situ. Axial translation of an expansion actuator may selectively radially expand the inner and outer shearing members concurrently.

A distally oriented occlusion penetrator may be disposed adjacent the distal end of the shearing members. The occlusion penetrator may comprise one or more end cutters that rotate with the inner shearing member and are exposed distally of the outer shearing member to help advance the shearing members distally through occlusive material and within a body lumen. Alternative occlusion penetrators include a shaft extendable distally of the shearing members, the shaft axially oscillating through occlusive material without penetrating through a vessel wall. An intravascular ultrasound sensor can be used to measure thrombus, monitor thrombus removal, and/or verify the treatment.

It may also be desirable to attach a porous or non-porous coverings or coatings to at least one shearing member, particularly to the outer shearing member. Such a covering or coating may extend between the struts of a shearing member or positioning cage when the shearing member or positioning cage expands, and can be made from PTFE woven material, filter material (metallic or polymeric), braid material (metallic or polymeric), mesh, polymeric coatings, and the like. The coatings can be applied to the outer basket through a dipping process. Alternatively, the coverings may be applied to the outer basket using cyanoacrylate or other adhesives, thread or suturing, welding or bonding, or the like. Such coatings may be disposed along a distal and/or proximal region of the expandable perforate shearing member, and may inhibit embolization of fragmented thrombus, constrain a treatment fluid or fluid stream, and the like.

In another aspect, the invention provides a thrombectomy catheter comprising a flexible tubular body having a proximal end and a distal end. A flexible drive shaft is rotatably disposed within the tubular body. An outer shearing member attached near the distal end of the tubular body has a circumferential series of independently flexible outer struts with inner surfaces. An inner shearing member is rotationally driven by the drive shaft within the outer member, the inner member having a circumferential series of independently flexible inner struts, the inner struts having outer surfaces which slide across the inner surfaces of the outer struts when the inner shearing member rotates, at least one member of the group comprising the inner struts and the outer struts being helically oriented.

Optionally, the inner and outer shearing members can each have proximal portions and distal portions, the struts of each shearing member affixed together at the proximal and distal portions and extending independently therebetween so that the shearing members flex axially primarily along the struts. A proximal housing may be coupled to the tubular body, the housing having a motor drivingly engaging the drive shaft. The drive shaft may engage the distal portion of the inner shearing member and be axially translatable relative to the outer tubular member from adjacent the proximal housing. An axial bearing surfaces of the outer and inner shearing members can cooperate to effect concurrent radial expansion of the inner and outer shearing members when the drive shave translates axially.

In another aspect, the invention also provides a method for forming a thrombectomy catheter. The method comprises providing a first tube having a proximal end and a distal end with a central region therebetween, the tube comprising a tube material. The central region of the first tube is cut axially so as to define a circumferential series of independent deformable struts, the struts comprising the tube material. The first cage can be positioned coaxially with a second resiliently deformable cage, and a drive can be attached for rotating at least one of the cages within a blood vessel for shearing of thrombus between the cages.

In another aspect, the invention comprises a method for removing thrombus from a blood vessel of a patient. The method comprises introducing a distal portion of a catheter into the blood vessel. The distal portion of the catheter is positioned adjacent the thrombus from outside the patient by manipulating a flexible body of the catheter. Inner and outer shearing members of the catheter are radially expanded within the blood vessel, the inner shearing member is rotated within the outer shearing member to shear the occlusive material therebetween.

BRIEF DESCRIPTION OF THE DRAWINGS

FIG. 5 is a perspective view of a tube cut so as to form the inner or outer basket of the catheter of FIG. 1.

FIG. 6 illustrates a flat pattern of the basket of FIG. 5, showing variable pitch of the helical struts.

FIG. 7 is a perspective view of an alternative basket having protrusions and/or circumferential indentations to inhibit axial sliding of thrombus during shearing.

FIG. 8 is a perspective view of yet another alternative basket having circumferential proximal and/or distal web members between struts to inhibit severing of valves and other structures disposed axially of the shearing baskets.

FIGS. 18A and 18B illustrate alternative embodiments of the positioning cage catheter device of the present invention.

FIGS. 22, 23, and 24A–24B illustrates steps in methods for use of the system of FIG. 20 for accessing a treatment site of an occlusion which is challenging and/or impossible to traverse with a standard guidewire.

FIGS. 25A–25C illustrates method of treating luminal occlusions in which a treatment region of the lumen is at least partially isolated.

DESCRIPTION OF THE SPECIFIC EMBODIMENTS

Figure 1:
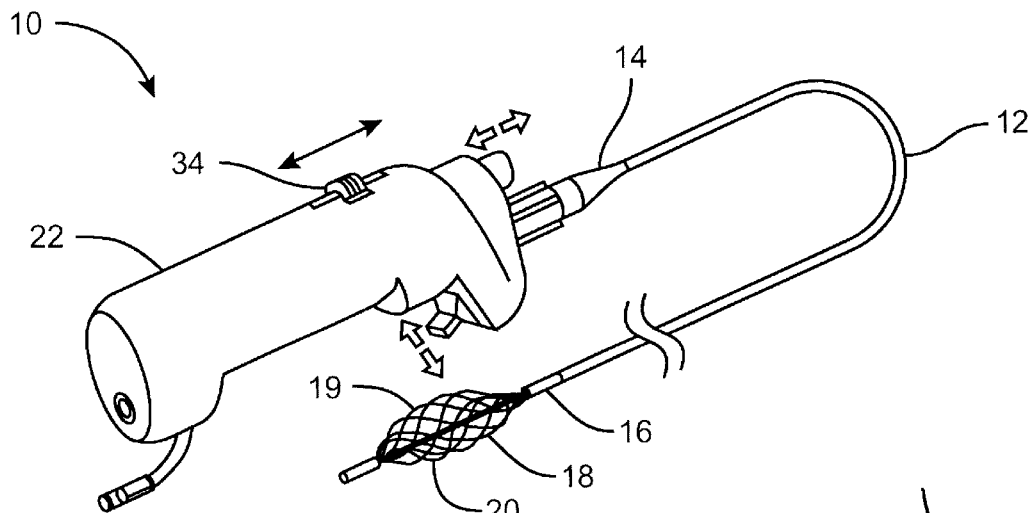
FIG. 1 is a perspective view of a thrombectomy catheter having a rotationally driven inner basket which cooperates with a outer basket to shear thrombus therebetween.

Referring now to FIG. 1, a vascular obstruction removal catheter 10 generally includes an elongate flexible catheter body 12 having a proximal end 14 and a distal end 16. Cooperating inner and outer shearing baskets 18, 20 define shearing means 19, and are disposed near distal end 16 of catheter body 12, while a proximal housing 22 is disposed near proximal end 14 of the catheter body. More specifically, outer basket 20 will typically be affixed at distal end 16 of catheter body 12, while a drive shaft drivingly couples inner basket 18 to a drive motor of proximal housing 22.

Figure 2:
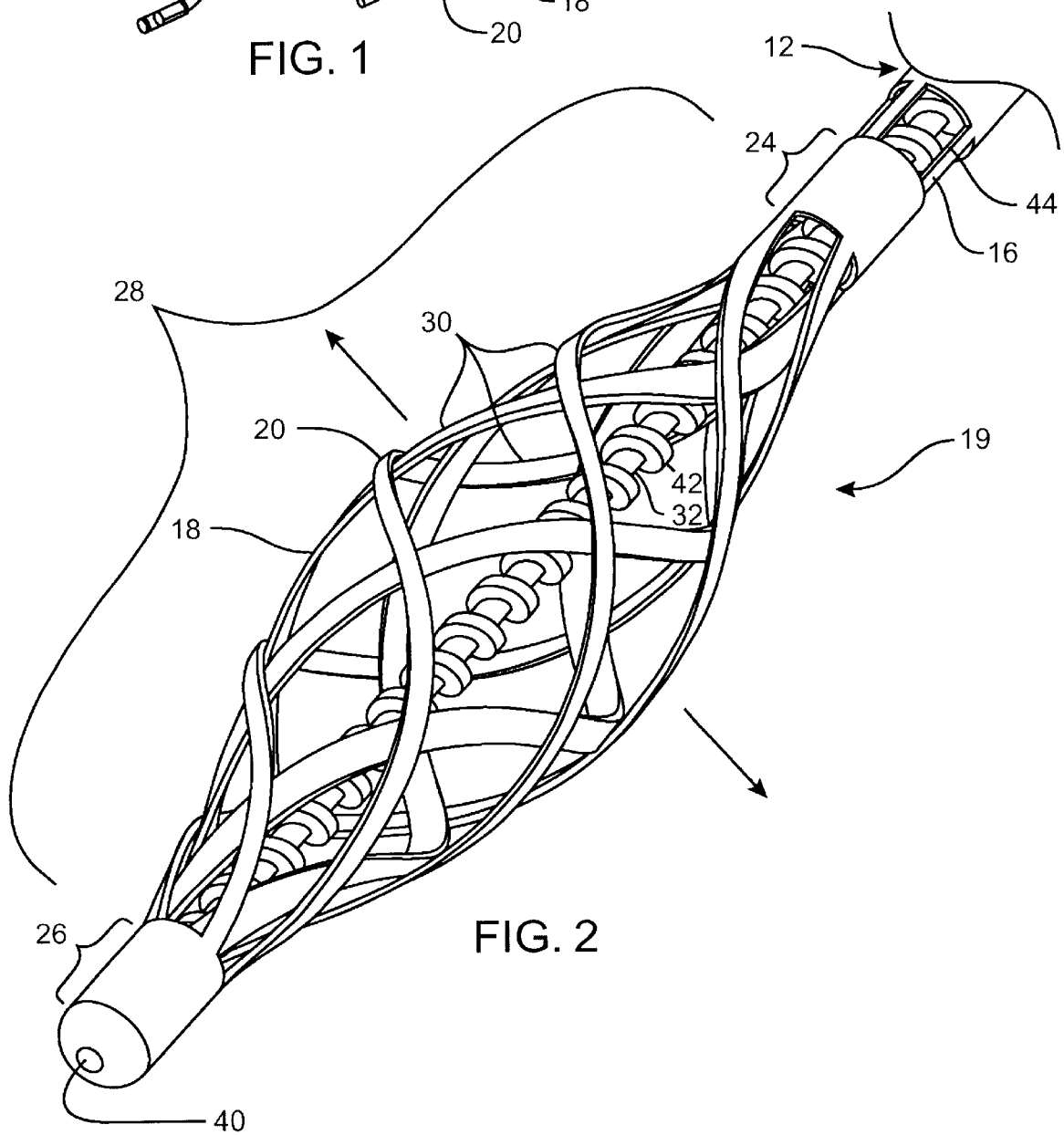
FIG. 2 is a perspective view of the distal portion of the catheter of FIG. 1.
Figure 3A:
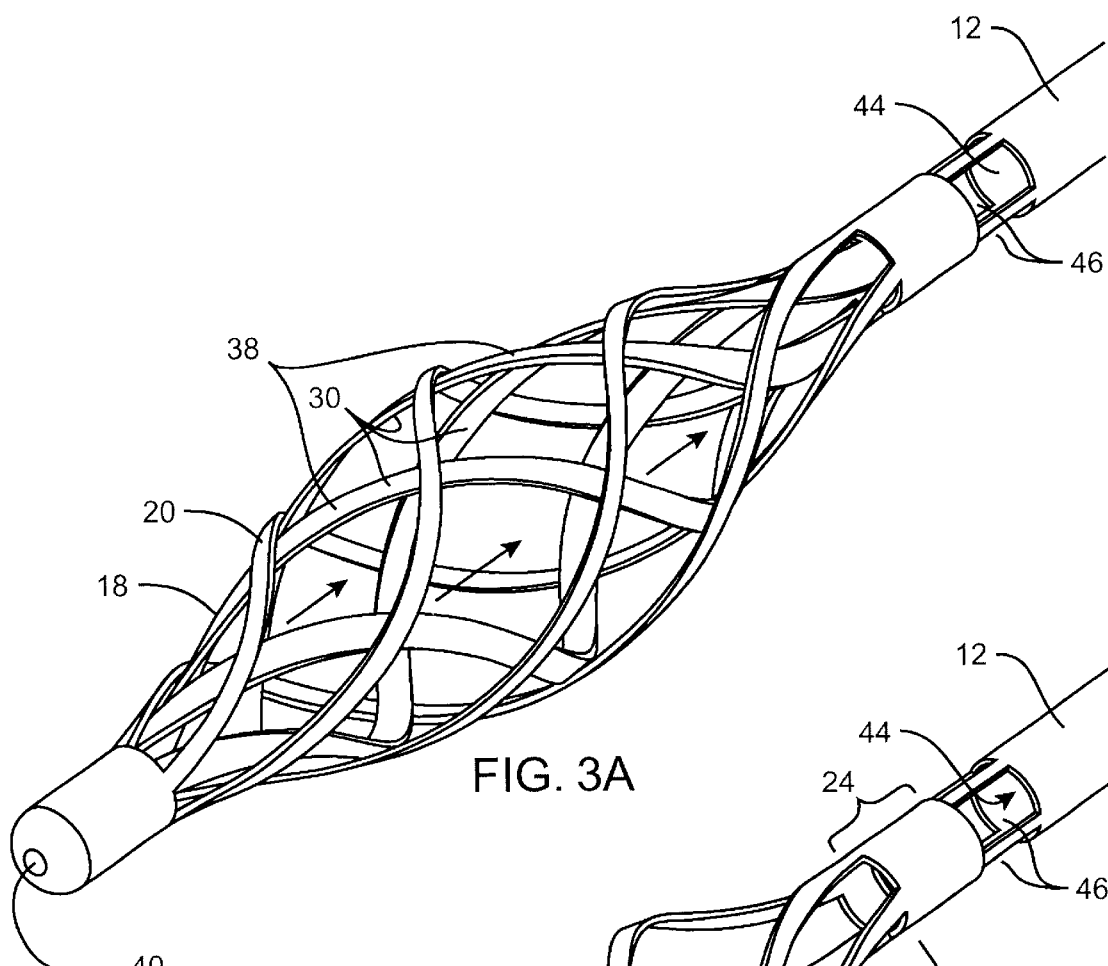
FIGS. 3A–3C is a perspective view showing the inner and outer baskets of the catheter of FIG. 1. 3B and 3C show how the outer basket may have a coating or covering for embolic capture.
Figure 4:
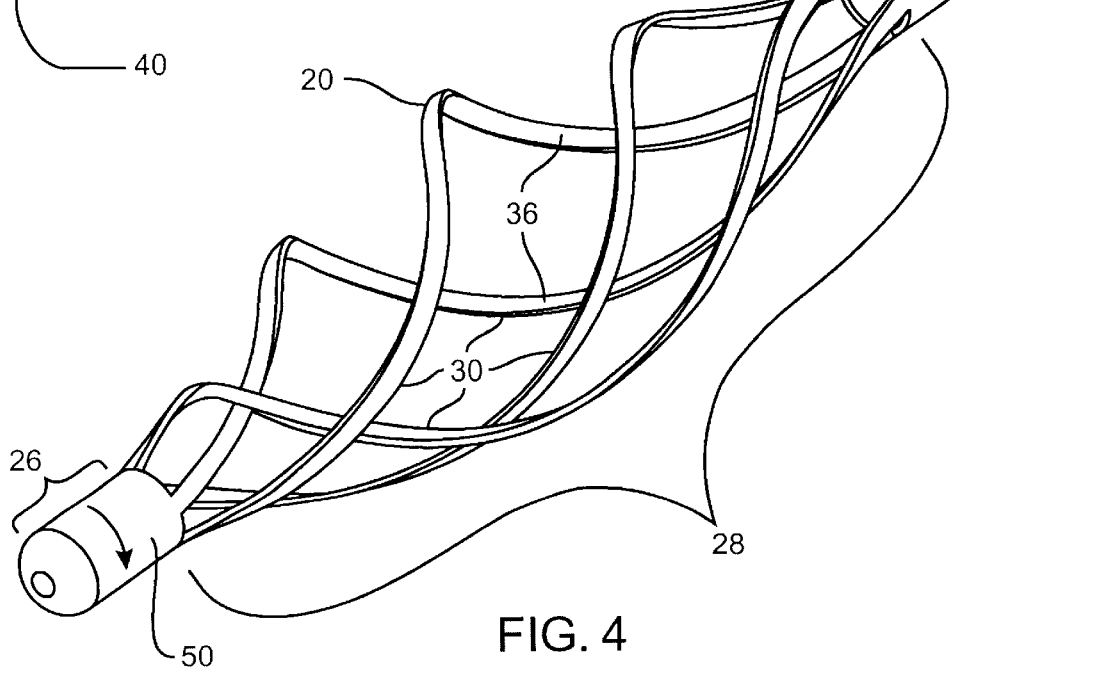
FIG. 4 is a perspective view of an outer basket or shearing member of the catheter of FIG. 1.

The inner and outer baskets 18, 20 of shearing means 19 are illustrated with some of the adjacent structures in FIG. 2, and in a simplified format (without some of the adjacent structures) in FIG. 3A. Outer basket 20 is shown without inner basket 18 in FIG. 4.

Each of the baskets 18, 20 includes a proximal portion 24, a distal portion 26, and an intermediate portion 28. Intermediate portion 28 includes a circumferential series of helical struts 30. Struts 30 are affixed together at proximal portion 24 and distal portion 26, but generally extend independently therebetween. This allows struts 30 to flex individually, and allows the overall axis of each basket 18, 20 (as well as shearing means 19) to deflect laterally so as to accommodate axial curvature of the vasculature.

Baskets 18, 20 will generally be radially expansible in situ from a low profile configuration to a larger profile configuration. Baskets 18, 20 will often comprise a resilient or superelastic material, and may be biased to expand radially when released from a radially constraining sheath. As helically wound baskets exhibit radial expansion which is coupled with a decrease in axial length, manipulation of the axial lengths of the baskets may also be used to induce or control the radial expansion, so that baskets 18, 20 may expand resiliently when released from an axial elongation restraint.

The baskets may also be biased toward a profile which is smaller than a fully radially expanded configuration, so that radially and/or axial restraints are used to actively expand the diameter of shearing means 19. In other words, by decreasing the length of baskets 18, 20, struts 30 may be pushed radially outwardly. In the exemplary embodiment, inner and outer baskets 18, 20 will expand radially when an axial actuator 34 of proximal housing 22 (see FIG. 1) is actuated from outside the patient body, as will be described hereinbelow. Hence, struts 30 may optionally be biased toward the radially expanded configuration, a low-profile configuration, or some configuration therebetween. Advantageously, the profile of shearing means 19 can be selected from a plurality and/or continuous range of expanded sizes, and can be varied during treatment.

Outer basket 20 may be rotationally coupled to catheter body 12. Thus, movement of the outer basket within the vasculature can be substantially limited to, for example, axial positioning and advancement of the shearing means for treatment, thereby inhibiting excessive trauma to the surrounding vessel wall. Optionally, additional manipulation of catheter body 12 may be used to abraid the vessel wall with direct engagement between the outer basket and the endothelium.

Struts 30 of outer basket 20 have continuous inner surfaces 36 between proximal portion 24 and distal portion 26. Similarly, struts 30 of inner basket 18 may have continuous outer surfaces 38 between the proximal and distal portions. By rotationally driving inner basket 18 within outer basket 20 using drive shaft 32, outer surfaces 38 slide across inner surfaces 36 so as to shear thrombus within the vasculature therebetween. In some cases, direct engagement between the inner basket and the thrombus between the struts of the outer basket may also provide some shearing and/or abrasion.

The drive shaft may be axially coupled to both the inner and outer baskets at distal portions 26. This allows concurrent and coordinated radial expansion of the inner and outer baskets so as to maintain sufficient proximity between the inner surface 36 and the outer surface 38 to provide the desired shearing effect. In the exemplary embodiment, drive shaft 32 comprises a tube having a guide wire lumen 40 and an outer helical pumping element 42. As described in detail in U.S. patent application Ser. No. 09/590,915, previously incorporated herein by reference, rotation of such a helical pumping element within an aspiration lumen 44 of catheter body 12 can draw and/or pump severed fragments of occlusive material, debris, and fluid proximally into and/or through the catheter body. This actively pumped aspiration may draw fluid proximally from within proximal portions 24 of baskets 18, 20, and/or radially inwardly and then proximally through one or more aspiration windows 46 about catheter body 12.

In some embodiments, at least one of the inner and outer baskets 18, 20 may have struts 30 which extend, at least in part, substantially axially. Preferably, at least one of the baskets will have struts 30, which wind primarily toward a first circumferential orientation 50 as the struts proceed distally, as can be understood with reference to FIG. 4. Such a consistent winding direction can be used to consistently urge sheared thrombus proximally, as can be understood with reference to the arrows illustrated in FIG. 3A. As inner and outer surfaces 36, 38 slide against each other, material which is severed between these cooperating surfaces can be urged proximally when the inner basket is rotated relative to the outer basket in the proper direction.

Figure 3B:
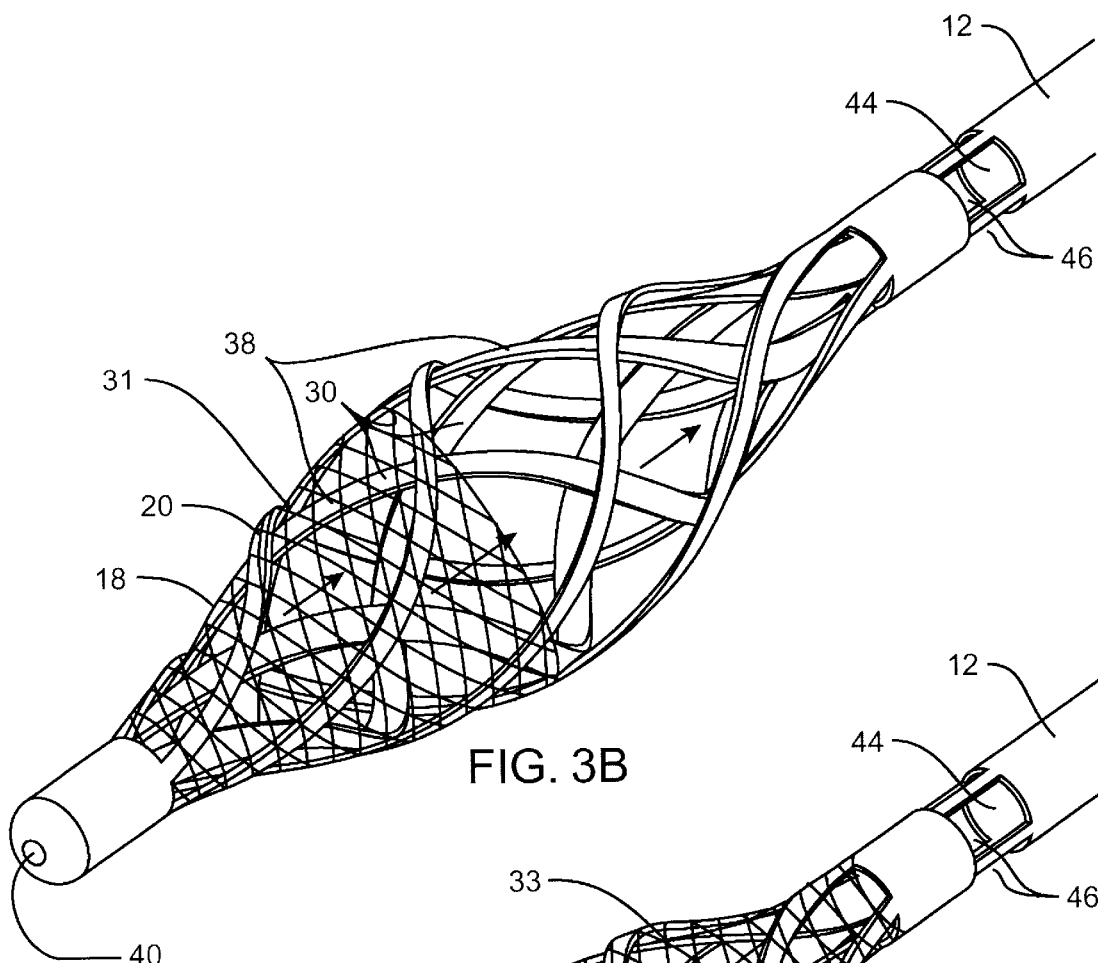
Figure 3C:
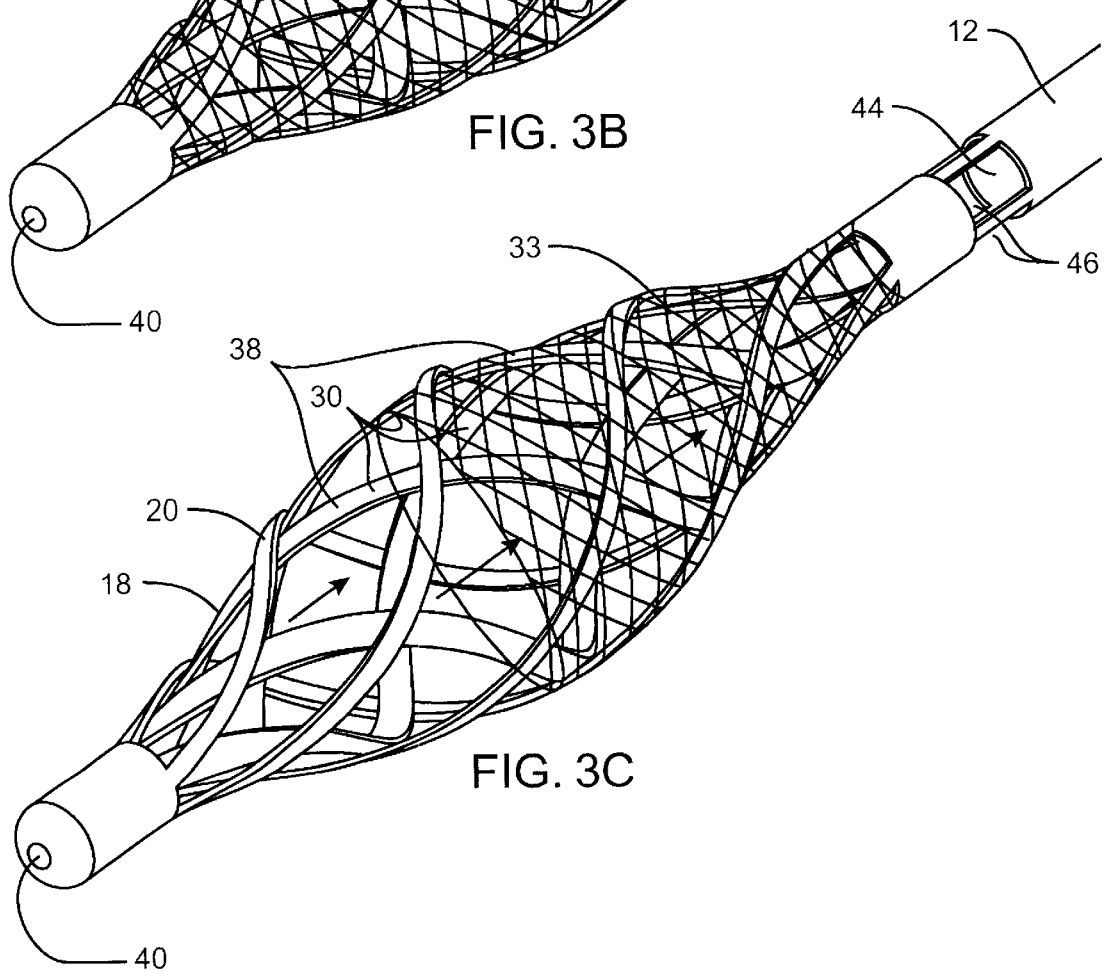

FIGS. 3B and 3C illustrate a catheter having a shearing means similar to that of FIG. 3A, and also having an expansible distal covering 31 (FIG. 3B) or an expansible proximal covering 33 (FIG. 3C). Coverings 31, 33 comprise a porous or non-porous coverings or coatings carried on (and expansible with) the outer shearing member along some (but typically not all) of the expansible portion of baskets 18, 20. Coatings 31, 33 may inhibit embolization of fragmented occlusive material, constrian a treatment fluid or fluid stream, inhibit injury to the venous valves and the like. Coverings 31, 33 extend between adjacent struts of a shearing member or positioning cage and accommodate radial expansion of the shearing member or positioning cage, the covering optionally being made from a PTFE woven material, filter material (metallic or polymeric), braid material (metallic or polymeric), mesh, polymeric coatings, and the like. The coatings may be applied to the outer basket through a dipping, filament winding or braiding process, or the like. Alternatively, the coverings may be applied to the outer basket using cyanoacrylate or other adhesives, thread or suturing, welding or bonding, or the like.

Referring now to FIGS. 5 and 6, an alternative basket structure is illustrated in a perspective view and as a flat pattern, respectively. The flat pattern of FIG. 6 graphically illustrates the configuration of the struts 30 as if basket 50 were cut along one side and unrolled. Such flat patterns are useful for fabrication and understanding the strut configuration.

As is clearly seen in FIGS. 5 and 6, a local helical wind angle defined between struts 30 and an axis 52 of basket 50 can vary along the axis. Preferably, a helical angle 54 along a central portion of struts 30 is significantly greater than a helical angle 56 near proximal and distal portions 24, 26. In other words, a pitch of struts 30 may vary locally along the axis of basket 50, with the pitch generally being greater adjacent the proximal and distal portions 24, 26. In the exemplary embodiment illustrated in FIGS. 5 and 6, the pitch varies according to a sinusoidal function in which the period in the central ⅓ of the axial strut length is ½ the period on the proximal and distal thirds. Advantageously, such enhanced central helical winding angles help to avoid circumferential distortion of struts 30 when axis 52 is deflected laterally, so that uneven separation between the struts during axial bending is inhibited.

Referring now to FIG. 7, at least one of inner and outer baskets 18, 20 may include struts 30 having one or more circumferential protrusions 62. Struts 30 of basket 60 can define pockets which effectively capture occlusive material against the struts of the cooperating basket. This can help avoid excessively axial sliding of material for which shearing is desired, as the material will be caught at a pocket or protrusion between the cooperating shearing struts. This can be understood by imagining a pencil which is to be sheared between the cooperating surfaces of a pair of scissors. The pencil may slide along straight cooperating shearing surfaces. Such sliding may be inhibited by forming a protrusion and/or pocket to capture the pencil along an edge of one or both shearing members.

A still further alternative basket 70 is illustrated in FIG. 8. In this embodiment, one or more circumferential members 72 extend between adjacent struts 30 adjacent proximal and/or distal portions 24, 26. Circumferential member 72 can allow some expansion at the ends, and can help inhibit entraining structures which are disposed axially of the shearing baskets. For example, circumferential member 72 may help avoid severing valves within blood vessels. A variety of alternative circumferential members might be used, including expandable and/or elastomeric webs, braided meshes, or the like.

The shearing baskets may be formed of a metal, optionally comprising a superelastic metal, such as Nitinol®, Elgiloy®, or the like. Alternative basket materials may include stainless steel or other high strength metals, and the baskets may comprise a polymer in some embodiments. Optionally, struts 30 may comprise wire with wire struts often being affixed at the proximal and distal portions 24, 26. In the exemplary embodiment, the shearing baskets are formed from a continuous material extending along proximal portion 24, along struts 30, and along distal portion 26. The struts may have a circumferential width in a range from about 0.004" to about 0.100", preferably having a width from about 0.006" to about 0.025". The radial thickness of the struts will typically be in a range from about 0.001" to 0.050", preferably being in a range from about 0.003" to about 0.025". The baskets may be formed by selectively cutting a tube so as to define the struts, often by use of photoetch processing, laser cutting, water jet abrasion, or EDM techniques.

Figure 9:
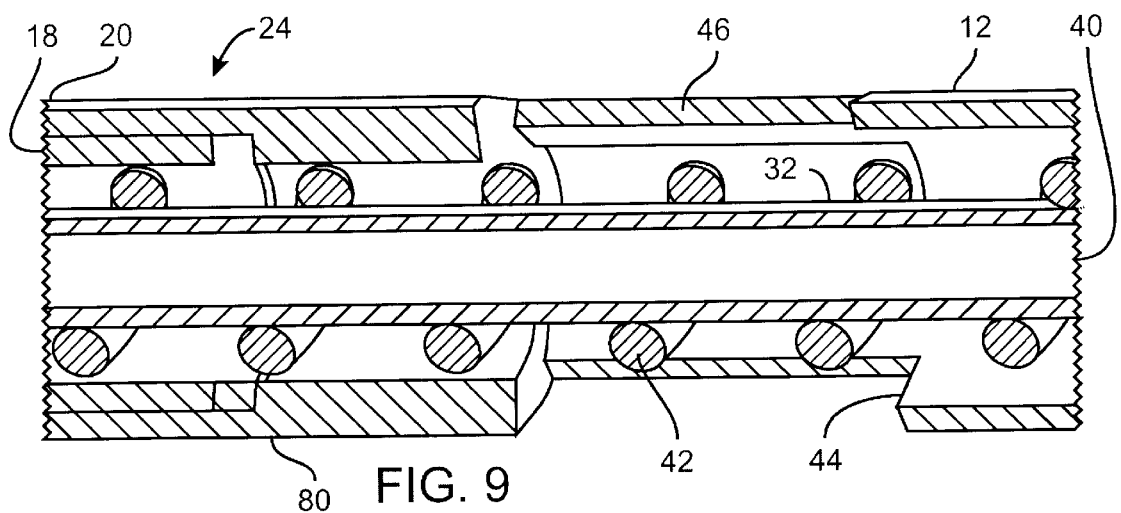
FIG. 9 is a cross-sectional view of the connection between the proximal end of the shearing baskets and the distal end of the catheter body.
Figure 10:
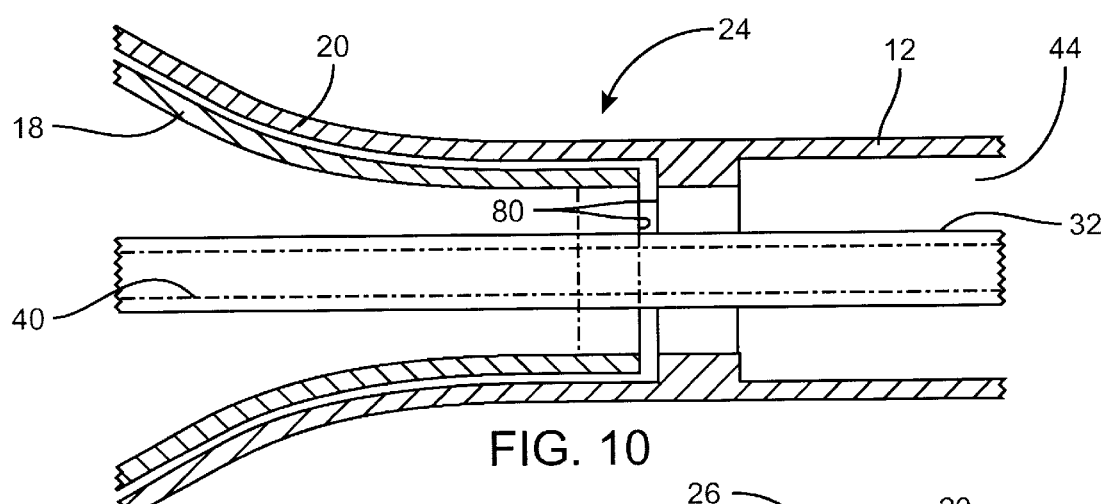
FIG. 10 is a simplified cross-sectional view of the proximal end of the shearing baskets and the distal end of the catheter.
Figure 11:
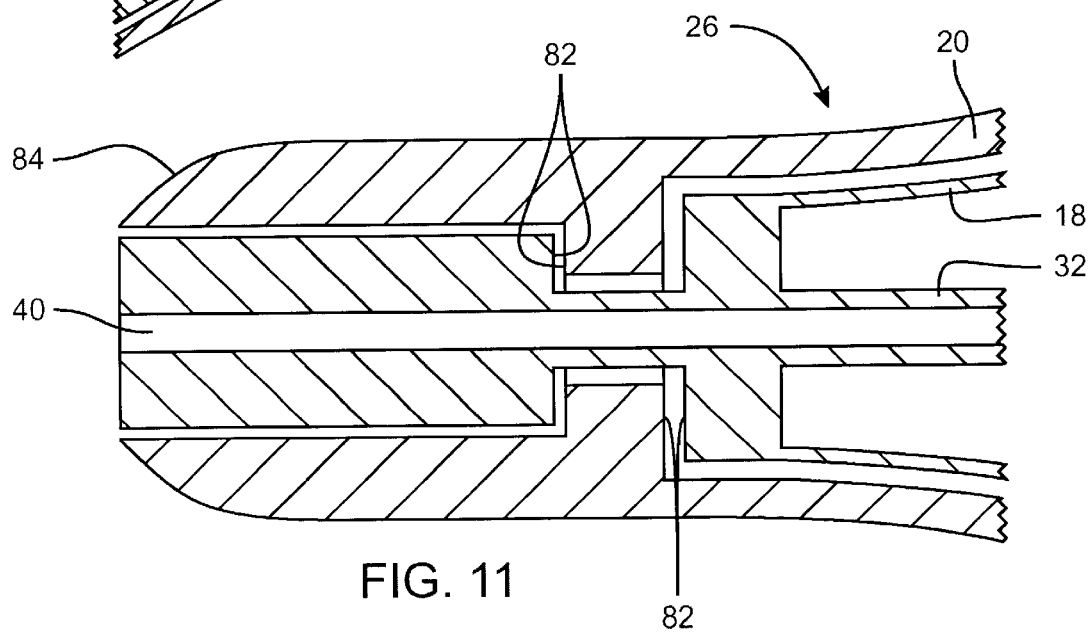
FIG. 11 is a cross-sectional view showing attachment of the inner shearing basket to a drive shaft.

Referring now to FIGS. 9–11, coupling of drive shaft 32 and catheter body 12 to inner and outer shearing baskets 18, 20 can be understood. Adjacent proximal end 24, catheter 12 is axially and rotationally affixed to outer basket 20, as illustrated in FIGS. 9 and 10. Drive shaft 32 rotates within aspiration lumen 44 of catheter body 12, and the drive shaft may have a helical pumping member 42. Pumping member 42 acts as an Archimedes screw, urging fluid and debris within proximal portion 24 of inner basket 18 proximally, and/or entraining fluid radially through aspiration windows 46.

Inner cutter 18 is rotationally affixed to drive shaft 32 adjacent portion 26, as illustrated in FIG. 11. Inner basket 18 is rotatable within proximal portion 24 of outer basket 20, and axial movement of the inner basket within the outer basket is limited by proximal cooperating thrust bearing surfaces 80, as seen in FIGS. 9 and 10. Similarly, distal portion 26 of outer basket 20 is axially coupled to drive shaft 32 and inner basket 18 by distal thrust bearing surfaces 82, as illustrated in FIG. 11. A nose cone 84 presents an atraumatic distal tip adjacent the distal port of guidewire lumen 40.

Figure 12:
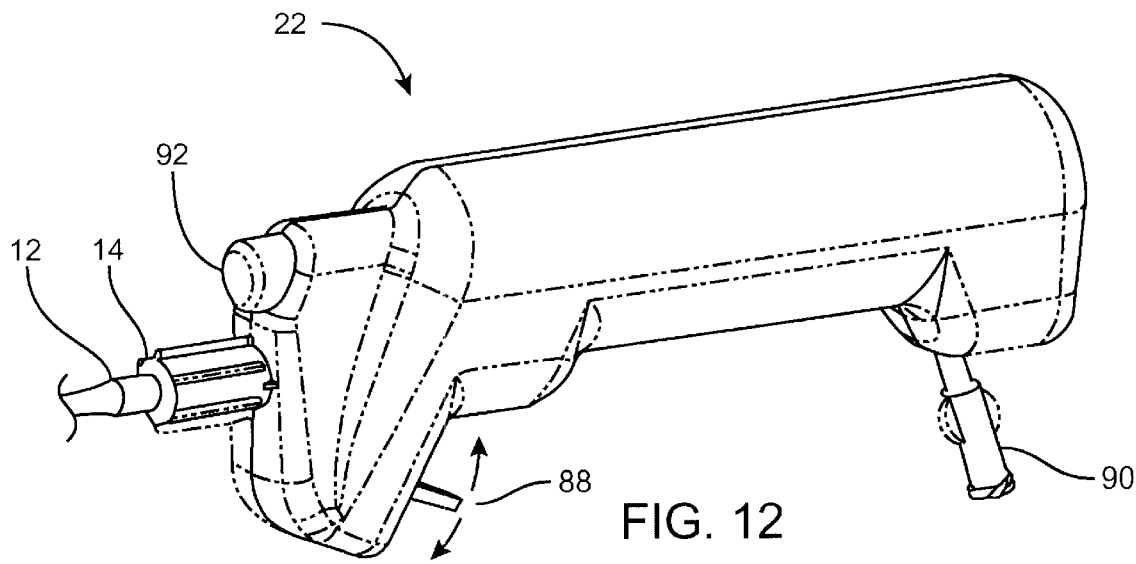
FIG. 12 is a perspective view of a proximal housing of the catheter of FIG. 1.
Figure 13:
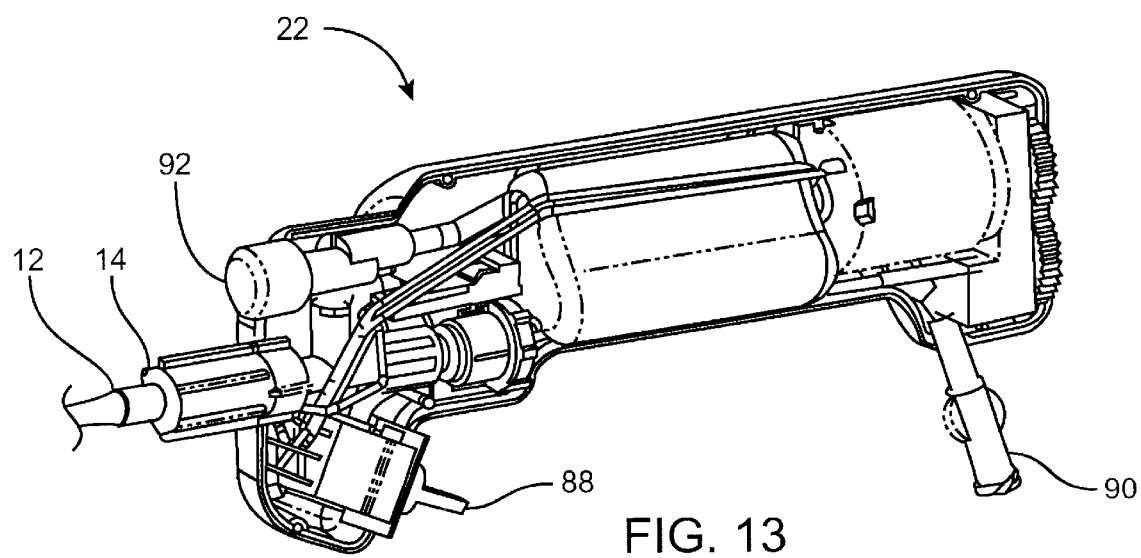
FIG. 13 is a perspective view of the housing of FIG. 12 with a portion of the cover removed to show the drive system and other internal components.
Figure 14:
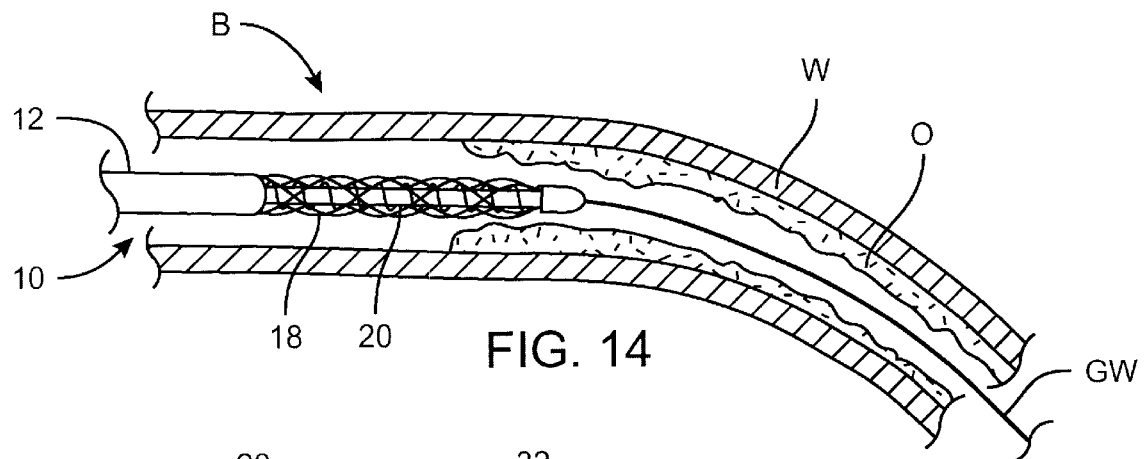
FIGS. 14–17 schematically illustrate the use of the thrombectomy catheter of FIG. 1.

As can now be understood with reference to FIGS. 9–11, rotation of drive shaft 40 results in rotation of inner basket 18 within outer basket 20. Translating drive shaft 40 proximally within catheter 12 can result in radial expansion of the shearing baskets, as the cooperating distal thrust bearing surfaces 82 decrease the overall length of the shearing baskets. Separate thrust bearing surfaces might be coupled to independently axially movable structures so as to effect independent radial expansion of the baskets The structure and use of proximal housing 22 can be more clearly understood with reference to FIGS. 12 and 13. Housing 22 contains a motor drivingly engaging drive shaft 32 within catheter body 12. The motor may be actuated by a drive actuator 88, with the drive actuator optionally effecting shearing motion of the inner basket and urging the sheared debris proximally when the actuator is moved in a first direction. When drive actuator is moved in a second direction, drive shaft 32 may rotate in an alternative direction, which may help free a jammed inner cutting member, or the like. An aspiration port 90 may be coupled to a vacuum source, such as a lockable syringe, a vacuum pump, or the like. A vacuum actuator 92 may provide momentary aspiration. Linear actuation of the drive shaft 32 may be provided by a linear actuator 34 (See FIG. 1)coupled to the drive shaft using thrust bearings and axially slidable engagement of drive splines, or the like.

Referring now to FIGS. 14–17, catheter 10 will generally be introduced into a blood vessel B over a guidewire GW using a conventional percutaneous or cut-down technique. Optionally, a portion of the blood vessel encompassing the target occlusive material may be isolated from surrounding blood flow. Such isolation may be provided by using a balloon guidewire and/or a sheath disposed around catheter body 12, with the sheath having an expandable member such as an annular balloon. Hence, isolation may be provided proximally and/or distally of an occlusive thrombus or other material O within a blood vessel wall W. Inner and outer baskets 18, 20 may be inserted and positioned adjacent the targeted thrombus or occlusive material O while the baskets are in a low profile configuration, optionally using a remote imaging modality such as fluoroscopy, ultrasound, or the like.

Figure 15:
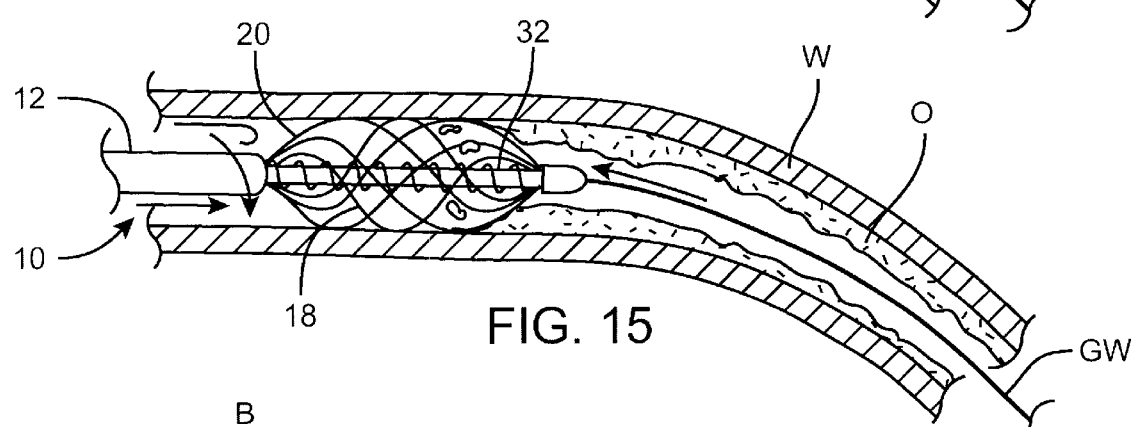

As illustrated in FIG. 15, once catheter 10 has been appropriately positioned, drive shaft 32 may be translated proximally relative to catheter body 12 so as to radially expand inner and outer baskets 18, 20. Where the inner and outer baskets are biased to expand resiliently, drive shaft 32 may be released to allow the baskets to expand. Where the baskets are biased to a configuration smaller than the desired deployed configuration, the drive shaft may be urged proximally relative to catheter body 12 so as to overcome the resilience of the basket structures. Advantageously, the overall size of the cooperating shearing members may be selected by selectively axially positioning the drive shaft relative to the surrounding catheter body. This helps provide accurate control over the depth of material sheared from wall W.

Once the positioned catheter is properly expanded to the desired size, rotation of the inner basket 18 is initiated by actuation of drive actuator 88 of the proximal housing 22. This results in both shearing of occlusive material O from wall W, and in urging of the severed debris in a proximal direction (effected both by the crossing angle of the struts 30 and pumping of the helical member of drive shaft 32. An aspiration pressure differential may also be applied via proximal housing 22 as described above so as to avoid release of debris within the blood vessel.

Figure 16:
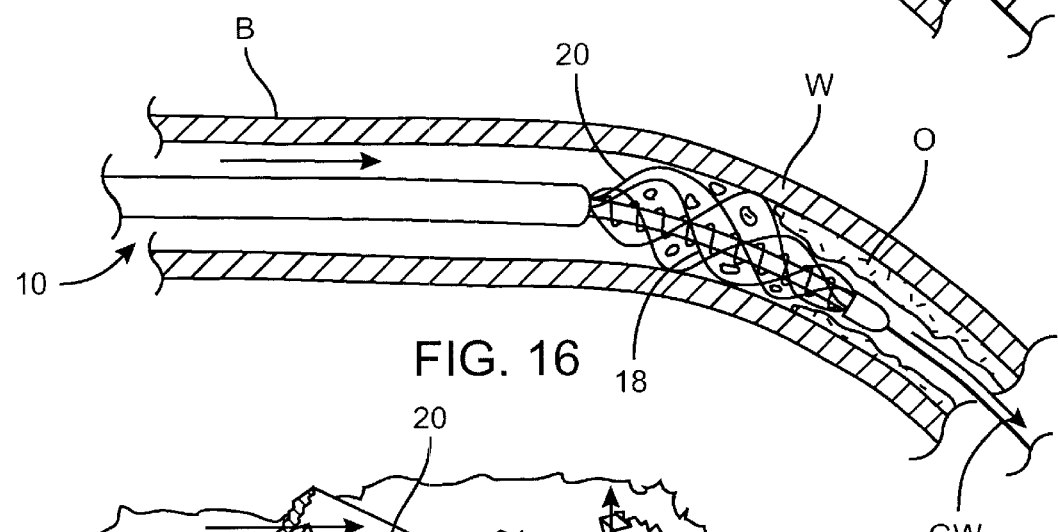

As illustrated in FIG. 16, catheter 10 may advanced distally over guidewire GW within the vessel wall W during rotation of inner basket 18. Outer basket 20 slides distally against the vessel wall substantially without rotating, thereby providing an incremental and controlled shearing action which can follow axial bends of the natural or artificial blood vessel B. The amount of occlusive material O removed form vessel wall W at a particular location may depend on the expanded size of the cooperating shearing baskets at that location, on the speed of rotation of the inner basket, on the speed of axial translation of the shearing means, and on the total time and number of rotations of the inner basket at that location.

Figure 17:
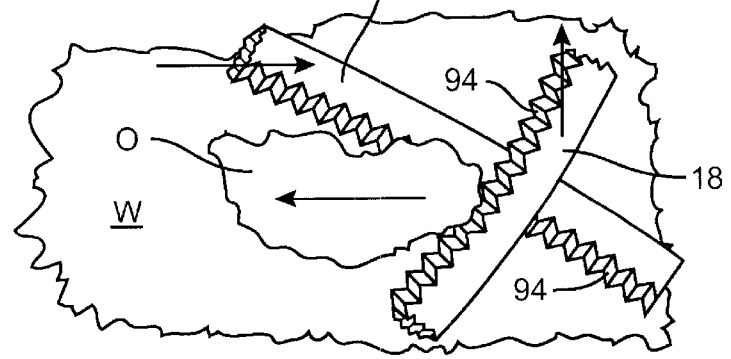

For relative soft occlusive material O, such as clot material, the proximal shearing action of the struts may, at least in part, draw the occlusive material proximally from along the vessel wall into the interior of the baskets, as can be understood with reference to FIG. 17. Similarly, rotation of the helical struts 30 of inner basket 18 may help draw catheter 10 distally within blood vessel B.

As can be understood with reference to FIG. 17, serrated circumferential surfaces 94 may improve shearing efficiency by limiting sliding of occlusive material O. Regardless, as the strut of inner basket 18 rotates relative to the struts of outer basket 20, occlusive material O protruding into an interior of the baskets from wall W is both severed and/or urged proximally.

A variety of adaptations and modifications on the structures and methods described herein may be provided. For example, a kit may include some or all of the components of catheter 10 together with instructions for their use according to one or more of the methods described herein. Proximal end or distal portions 24, 26 of the inner and/or outer baskets may comprise a serpentine circumferential member, thereby allowing that portion to be expanded radially during assembly of catheter 10. It may be advantageous to at least slightly bias struts 30 radially outwardly so as to facilitate initial axial compression of the baskets. While the present invention has been described with reference to removal of clot, the structures and methods of the present invention may find applications for removing occlusive material from a wide variety of alternative body structures and lumens, including the fallopian tubes, genitourinary tract (for example, for treatment of benign prostatic hyperplasia, and the like), gastrointestinal tract, and the like.

A positioning cage catheter 120 which is particularly beneficial for treatment of blood vessels having a total occlusion (when it is difficult or impossible to access the entire treatment site with a standard guidewire) is illustrated in FIGS. 18A and 18B. Many of known intraluminal therapies require that (or are facilitated when) the lumen has a significant open cross section, without an excessively tortuous luminal path, to allow the guide structure to be placed across the occlusion.

It should be noted that the term total occlusion may refer to any substance or anatomic morphology that acts to severely occlude a body conduit such that it is difficult to pass a wire from proximal end of the occlusion to the distal end. Depending on the type of material occluding the body conduit (soft plaque, calcified plaque, thrombus, fibrin, clot, intimal hyperplasia, in-stent restenosis, fatty tissue etc.) some occlusions may be more severe than others but all are included in the scope of the present invention when there may be some difficulty passing a guidewire therethrough.

Cage 110 may be formed of multiple straight wires or struts 111, or multiple curved wires or struts 112 formed into a helix as depicted in FIG. 18B. It is noted that a double wire (not shown) may also be employed to form the cage structure. These cage structures are fixedly attached to a catheter body 113, having a distal tip 114 accommodating passage of a guidewire through lumen 115.

In an exemplary embodiment, catheter system 120 comprises a positioning cage such as described one of those described above, or such as those in related U.S. patent application Ser. No. 09/388,294, incorporated herein by reference. A guidewire such as the described in U.S. patent application Ser. No. 09/491,401 (vibrating guidewire) or U.S. patent application Ser. No. 09/005,217 incorporated herein by reference, or in some cases such as those readily available from various manufacturers (TERUMO, CORP./ BOSTON SCIENTIFIC, Natick, Mass, GUIDANT, CORP., Indianapolis, Ind., or PERCUSURGE, Sunnyvale, Calif.) may be used within catheter system 120, as will be understood from the following description. Optionally, the positioning cage and the treatment catheter may be employed as an integral unit to both place the guidewire, and to perform the subsequent treatment. In such embodiments a device such as those described in U.S. patent application Ser. Nos. 09/491,401 and 09/388,294 previously incorporated herein by reference, may be employed.

In use, the total occlusion access devices of the present invention may be inserted into a body conduit and advanced to the proximal side of the occlusion, either over a guidewire, or by just advancing the positioning cage to the treatment site, depending on the body lumen to be treated. Once at the treatment site, the positioning cage can be pushed against the occlusion. As will be described below, a guidewire or dottering device may be advanced from the cage through a lumen coaxial with the cage (and hence, substantially coaxial with the body lumen when the cage is expanded therein) to penetrate and/or pierce the occlusion. The combination action of the positioning cage asserting forces against the vessel wall and the occlusive material (optionally by rotating the cage or expanding the against the vessel wall), and the guidewire or dottering device probing against the occlusion, may work to tunnel the devices through the occlusion to the distalmost portion and beyond. The positioning cage may help to center the action of the dottering member and inhibit perforations through the vessel wall or other vessel wall damage.

The positioning cage may be part of a treatment catheter and therefore, once the guidewire is in place, the treatment catheter may be advanced to initiate removal of the occlusion. Depending on the occlusion to be treated, a distal protection device, such as a balloon fixed to a guidewire, a filter affixed to a guidewire, or the like, may be employed distal of the occlusion and expanded to minimize any embolization of clot or other material. In addition, an occlusion balloon or filter may be deployed proximal of the occlusion to isolate the lesion and allow the treatment device (or a separate structure) to infuse saline, contrast, pharmacologic agents such as tPA, ReoPro, IIB3A inhibitors and the like, or chemical ablation agents or acid solutions such as those described in PCT Application No. PCT/US99/15918 (WO 00/03651). The occlusive debris can be removed by activating the shearing, macerating, and aspirating function of the device of the present invention as described above, and in U.S. patent application Ser. No. 09/388,294 and U.S. Provisional Patent Application No. 60/154,752.

Referring now to FIGS. 18C–F, the structure of an exemplary positioning cage catheter system 120a adjacent distal tip 114 is illustrated in more detail. Catheter system 120a includes inner and outer shearing members in the form of baskets 18, 20, as described above, and can also include some or all of the catheter structures described above for selectively expanding the inner and/or outer baskets, for irrigating and/or aspirating fluids, for urging fluids and severed fragments proximally within the outer sheath, for isolating the body lumen proximally and/or distally of the shearing members, and the like.

To facilitate advancement of catheter system 120a distally for treatment of a total occlusion, a total occlusion penetrator is provided adjacent tip 114. In the embodiment of FIGS. 18C–F, the penetrator is in the form of a distally exposed morcellator 122. Morcellator 122 comprises a circumferential series of helical cutters which may be rotationally coupled to inner shearing member 18 or may rotate independently of the shearing member. The cutters of morcellator 122 may extend distally of the distal portion of the outer shearing member 20 and/or distally of the inner tubular body which defines the guidewire lumen 115 sufficiently to allow the rotating cutters to advance into the occlusive material of a total occlusion when the morcellator rotates. Expansion of the shearing member can maintain separation between the advancing morcellator and the vascular walls, so that the expanded shearing member acts as a positioning cage. As described above, use of a morcellator in the form of one or more helical structures within a lumen (the lumen here defined by the distal portion of outer shearing member 20) can act as a pump or Archimedes screw to urge the occlusive material proximally.

Figure 18C:
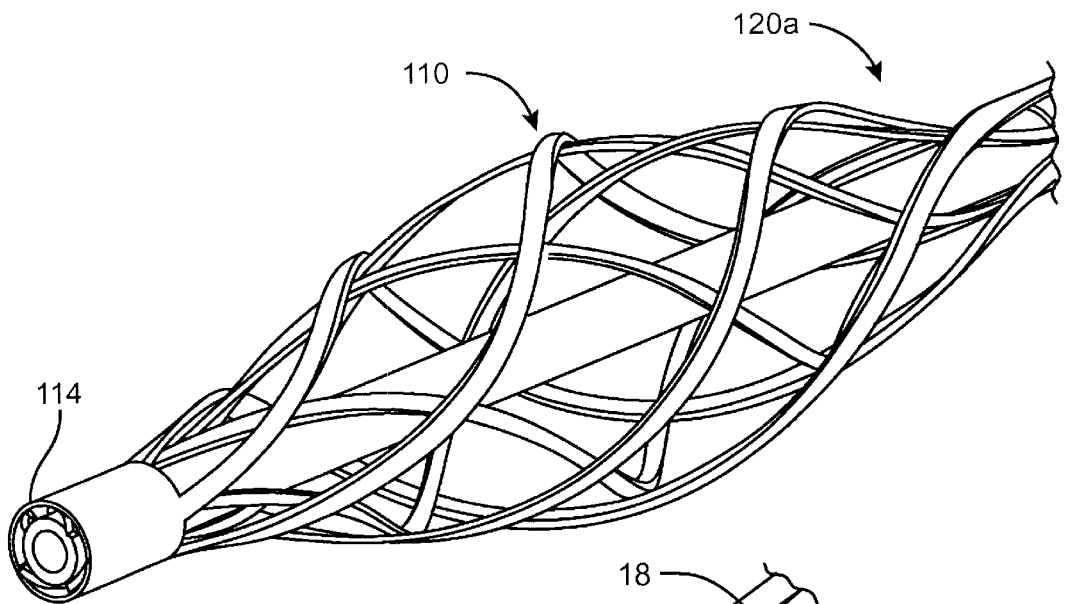
FIGS. 18C–18F illustrate radially expandable positioning and shearing structures having a thrombus penetrator in the form of a distally exposed morcellator for forming a passage through a total thrombus occlusion.
Figure 18D:
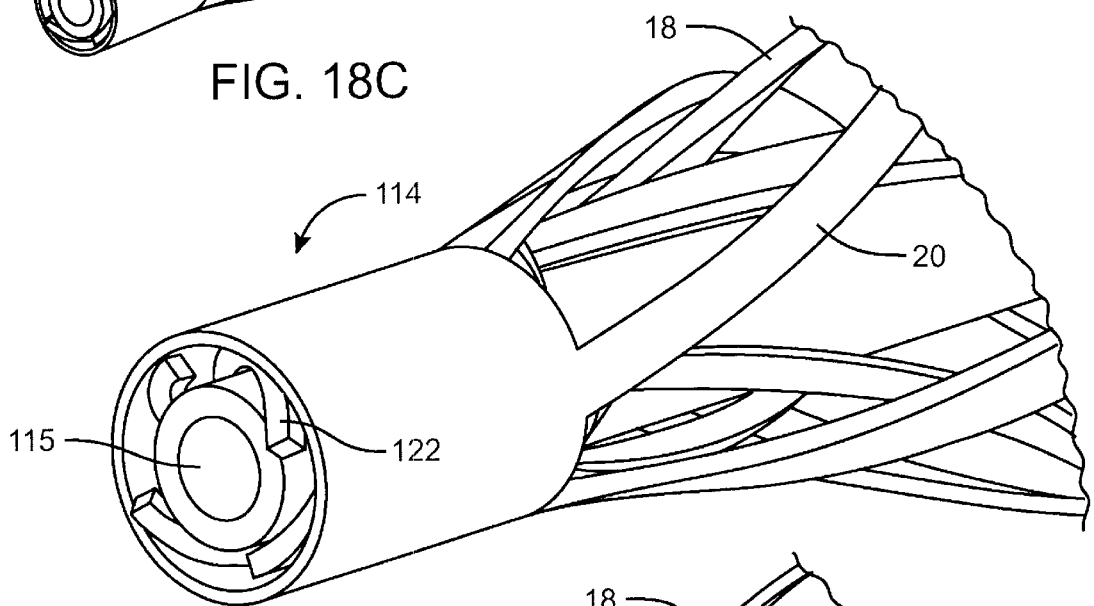
Figure 18E:
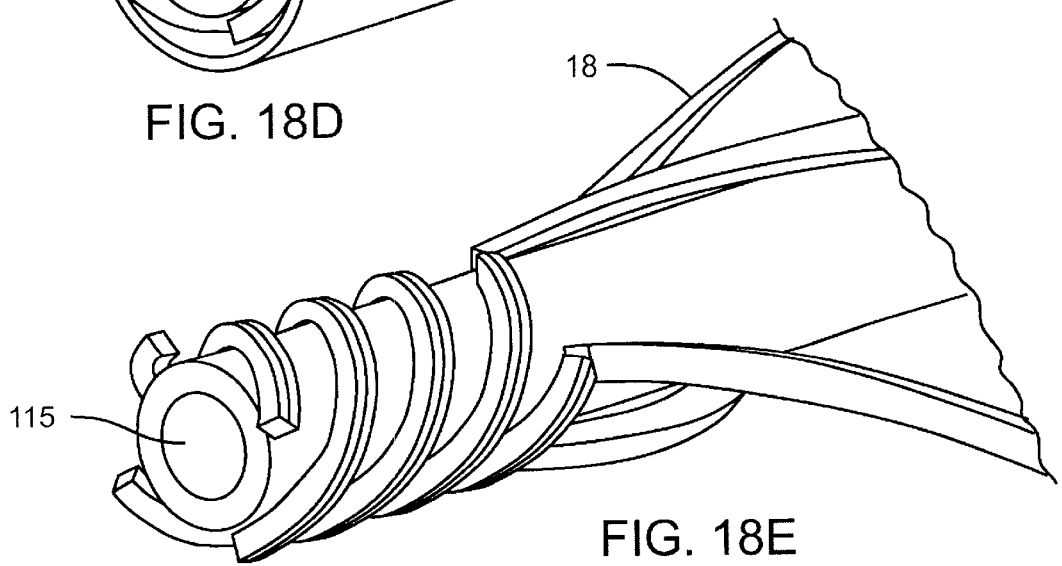
Figure 18F:
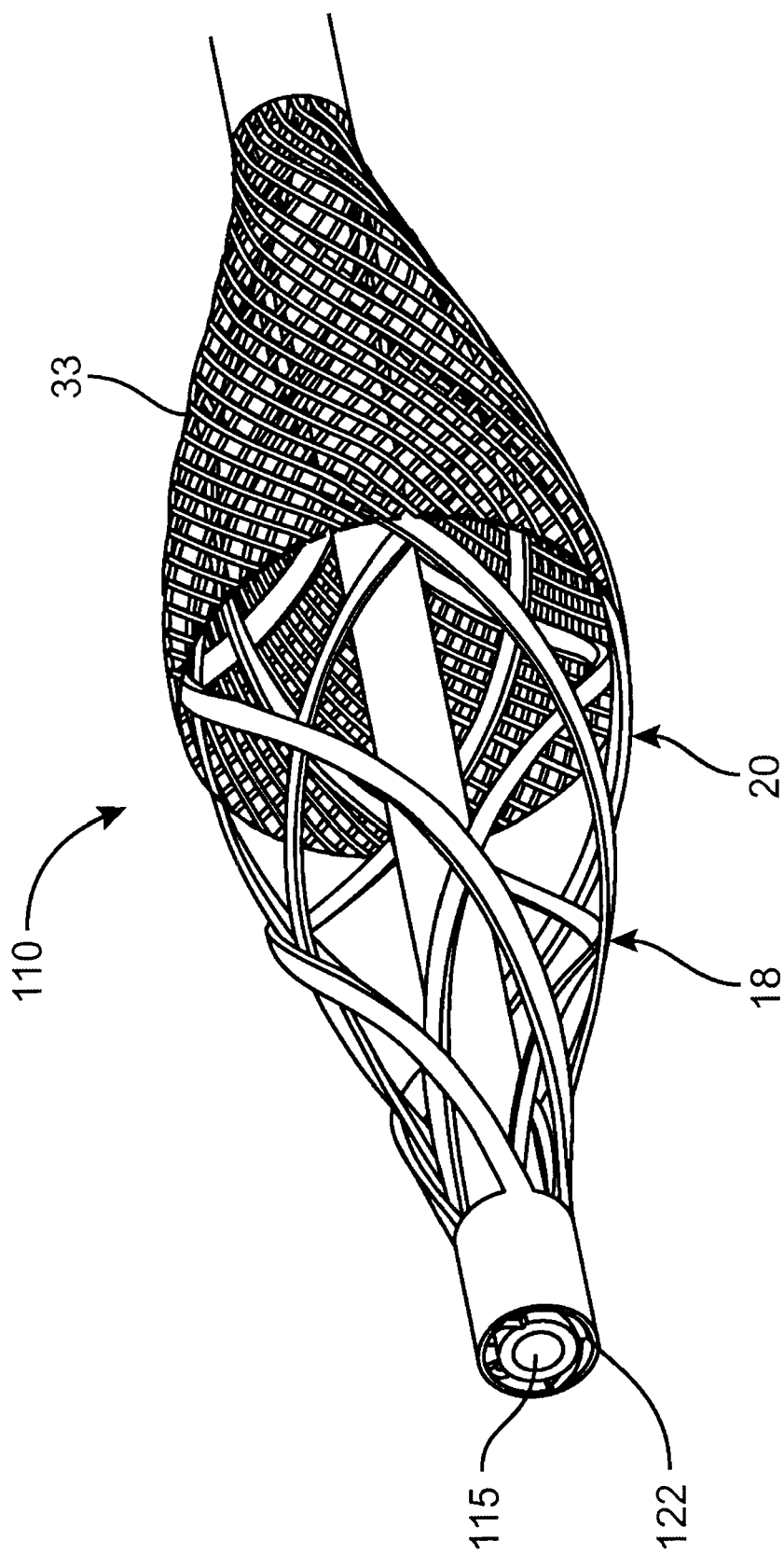
Figure 19:
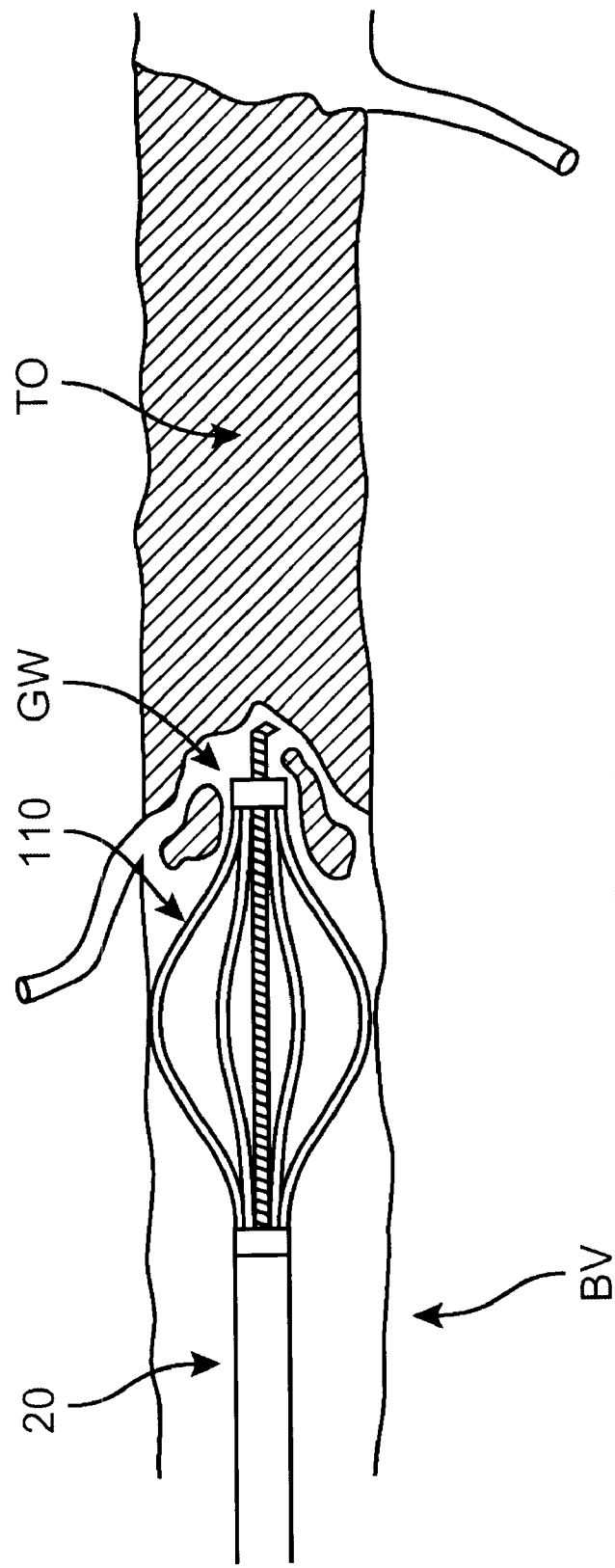
FIG. 19 illustrates the positioning cage catheter device of the present invention being used to initiate the crossing of a total occlusion.

In use (as illustrated in FIG. 19), the positioning catheter 120 is inserted into a vessel BV and advanced to the treatment site just proximal of total occlusion TO. Cage 110 may actually engage the occlusion TO and begin loosening the plaque or other material making up the occlusion. Furthermore cage may be manually rotated to further engage the occlusion. Once at the treatment site, guidewire GW may be optionally advanced out of the distal tip of the positioning catheter to contact and help fragment the occlusion TO, the guidewire optionally being adapted for use as an occlusion penetrator, as will be described below. As described above regarding FIGS. 18C–E, a morcellator 122 may also be used as an occlusive material penetrator by rotating the distally exposed morcellator and advancing the catheter system to engage the rotating morcellator against the total occlusion TO. Catheter 120, guidewire GW, and/or morcellator 122 may be used in combination or in an alternating motions or cycles to create a pilot hole through the occlusion TO such that the guidewire GW may be placed through the occlusion and advanced distally therebeyond.

Figure 20:
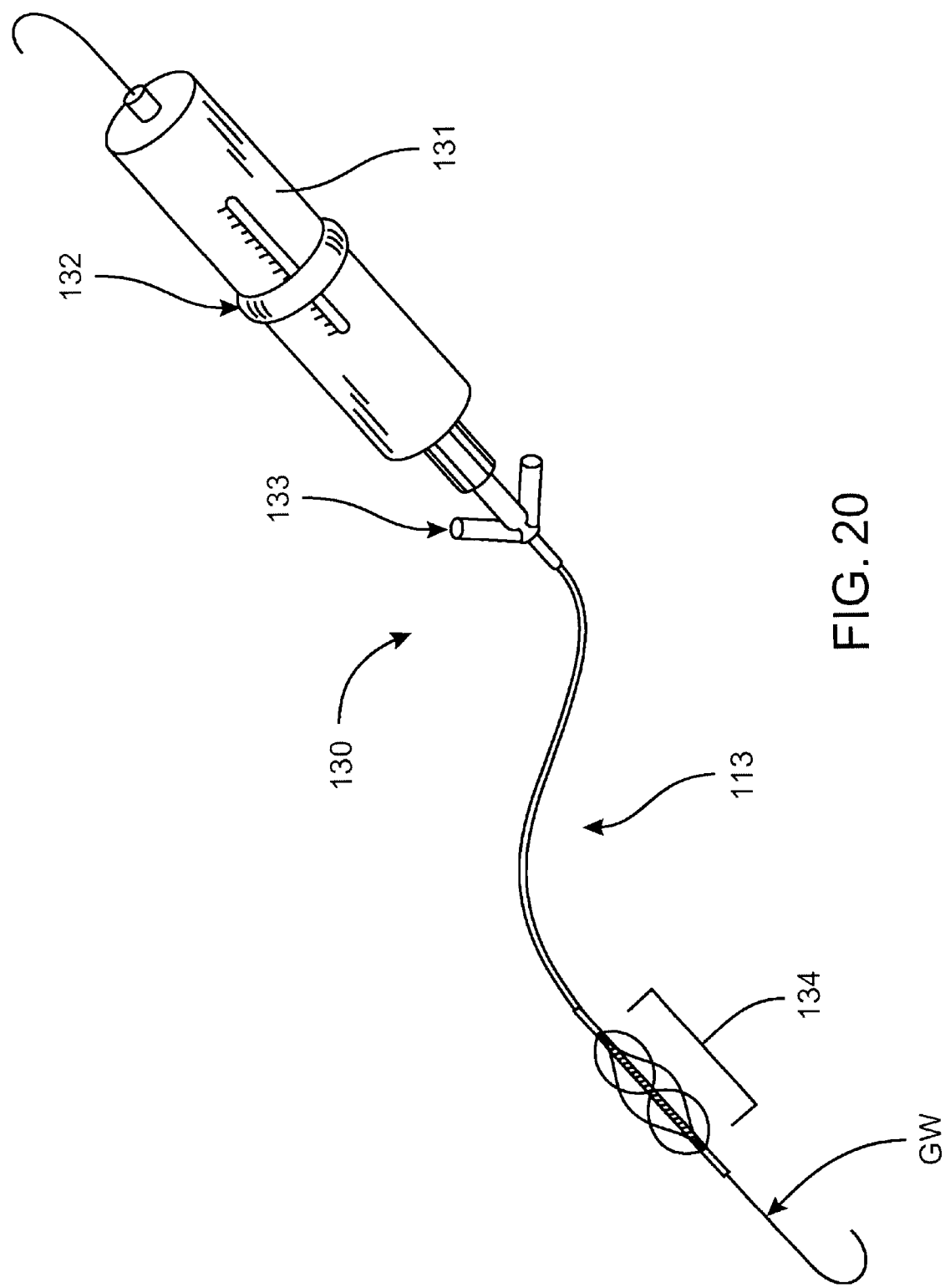
FIG. 20 illustrates an alternative embodiment of the present invention wherein a positioning cage and a treatment device are formed integrally and placed over a guidewire.
Figure 21:
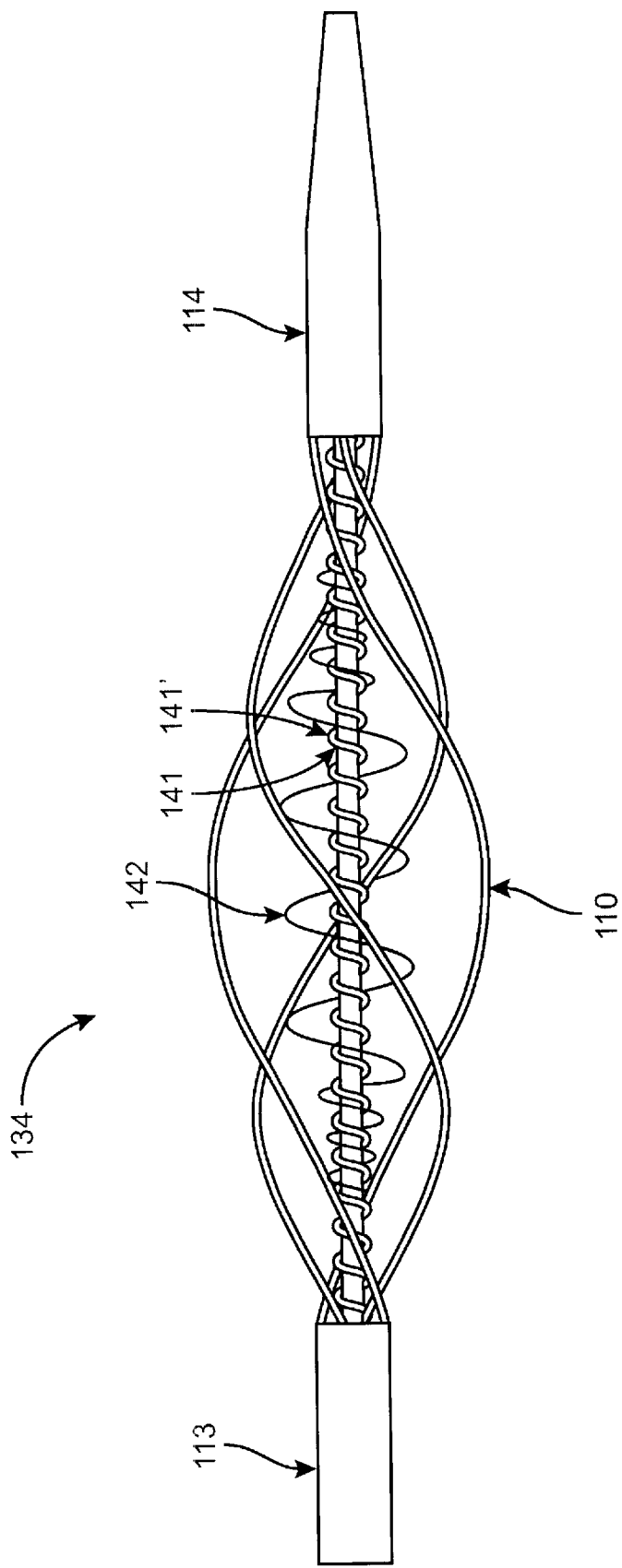
FIG. 21 illustrates details of the distal end of the integral positioning cage and treatment device of FIG. 20.

An alternative positioning cage catheter system is schematically depicted in FIG. 20. Treatment catheter 130 comprises a proximal end having a handle 131 with an actuator knob 132 and a Y connection 133 to allow infusion and/or aspiration. A catheter shaft 113 extends distally from handle 131 toward a distal working end 134. FIG. 21 depicts the distal working end of treatment catheter 130, showing a positioning cage 110 attached at its proximal end to catheter shaft 113, and on its distal end to distal tip 114. Distal working end 134 further comprises a drive shaft 141 with an optional coiled mechanical pump 141' and a macerator 142 coiled therearound. A more detailed description of treatment catheter 130 may be found in related case U.S. patent application Ser. No. 09/388,294 as previously incorporated by reference.

Figure 22:
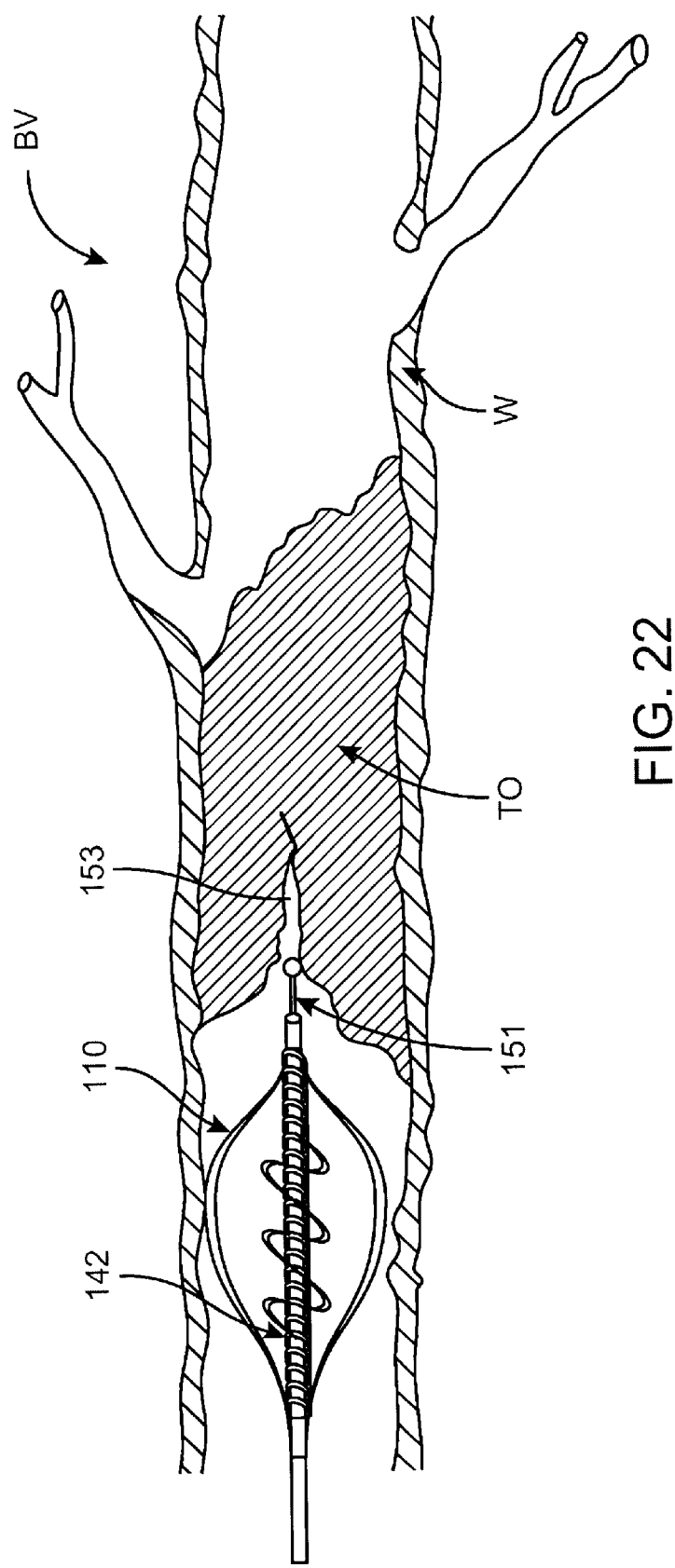

In use, as illustrated in FIG. 22, treatment catheter 130 is inserted into the lumen of a vessel BV and advanced to the proximal portion of the treatment site. At this point the lesion can either be crossed mechanically (as described above regarding FIG. 19) and/or saline or other therapeutic agents may be infused (optionally via guidewire lumen 115, as shown in FIG. 18) to assist in dissolving, softening, and/or fragmenting the occlusive material. In some embodiments, such agent flow from the catheter system alone may be sufficient to allow a standard guidewire to be advanced through the occlusion. The remaining components of the catheter system may then be advanced over the guidewire and remove some or all of the occlusive material, as described above.

A standard or modified guidewire may be used to help form a pilot hole or passage for placement of a guide structure. In the exemplary embodiment, a dottering tool or dottering guidewire 151 can be centered within the lumen of the blood vessel BV by expanding cage 110. The centered dottering tool 151 may then be used as an occlusive material penetrator by advancing the dottering tool in a linear translating and/or cycling motion to begin formation of a pilot hole or pathway through the total occlusion. Although dottering guidewire 151 may have a structure similar to a standard guidewire, the dottering tool will optionally have a more rigid construction than a standard guidewire adjacent the distal end, and the distal portion of the dottering tool may also be able to assume a straight configuration with sufficient axial column strength for advancement of an atraumatic tip distally from the guidewire lumen of the catheter system and into the occlusive material.

Once dottering tool 151 has formed a passage 153 through the total occlusion, other devices (such as standard guidewires, a balloon guidewire or other distal protection devices to inhibit embolisms and/or release of therapeutic agents distally of the total occlusion, and the like) may be advanced through the passage, or the dottering wire may be used as a guide structure.

Figure 23:
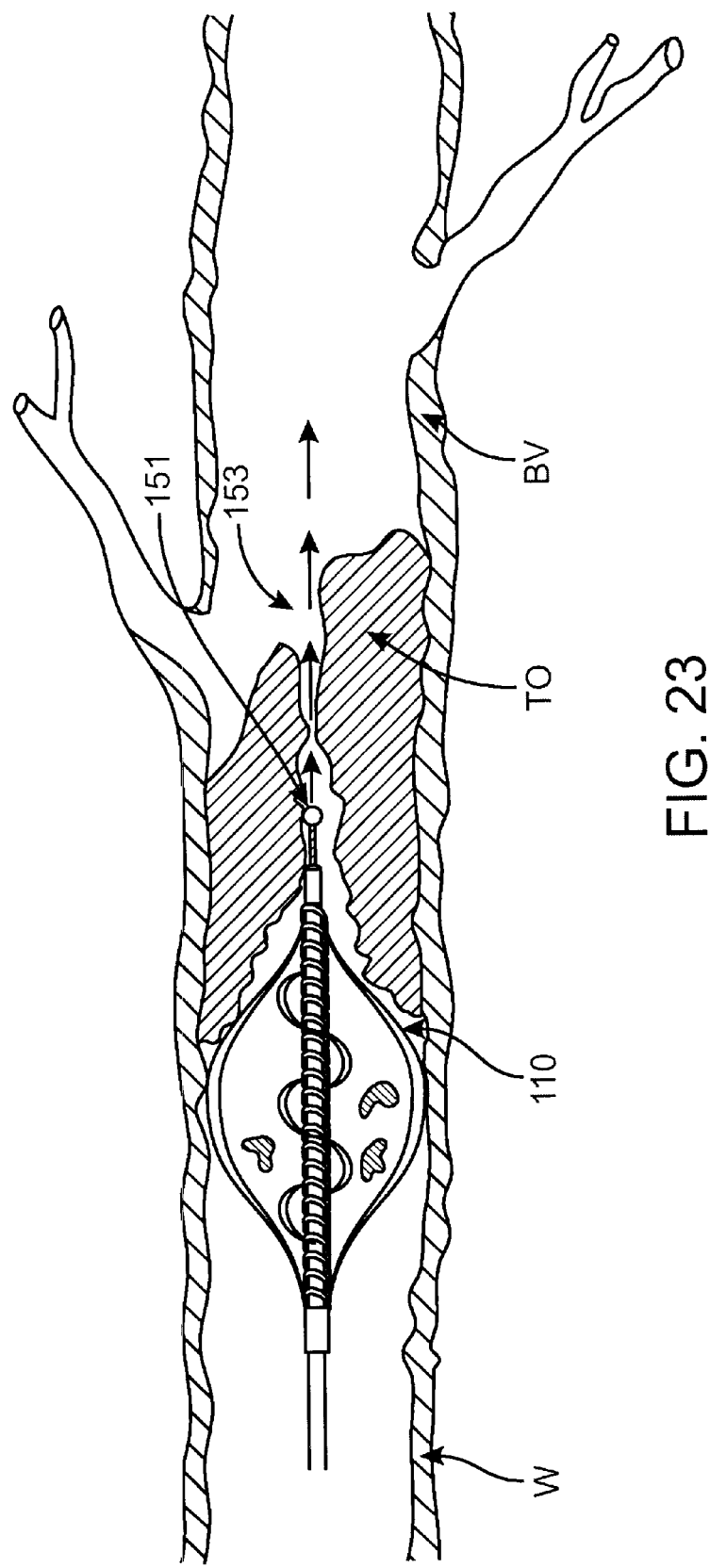

Referring now to FIGS. 22 and 23, centering cage or basket 110 can provide centering of guidewire lumen 115. Centering of this coaxial lumen can help protect the vessel wall from mechanical injury imposed by dottering device 151. Dottering device 151 may be cycled axially mechanically or using an axial drive motor, and may also be rotated manually or by drive motor. The centered guidewire lumen, which should be substantially coaxial with the vessel, may also be used for infusion of any of a variety of fluids. It may be advantageous to locally deliver (via guidewire lumen 115 or via some other infusion pathway) a thrombolytic agent having an enzymatic action with breads down fibrin clot matrix (such as Alteplase, tPA, Activase, Tenecteplase, TNK, and TNKase from Genentech, Inc.; Anistrpelase a-SK, and Eminase from Roberts Pharmaceuticals; Reteplase, r-PA, and Retavase from Centocor, Inc.; Streptokinase, SK, and Streptase from AstraZeneca, Inc.; and/or Abbokinase, from Abbott, Inc. In some embodiments, a GP IIb/IIIa inhibitor, which inhibits the fibrogen binding site of platelet membrane, may be locally delivered. Suitable GP IIb/IIIa inhibitors may include Abciximab and ReoPro from Centocor, Inc.; Tirofiban and Aggrastat from Merck, Inc.; Eptifibatide and Integrelin from Cor Therapeutics, Inc.; Bitistatin, Kistrin, and Aspirin. Still further active agents might be used, including anti-thrombin agents and agents directed toward prevention of restenosis (to inhibit coagulation and/or decreasing smooth muscle proliferation and migration), such as Heparin, LMW, enoxaparine or Lovenox, dalteparin or Fragmin, ardeparin or Normoflo, Hirudin, Argatroban, PPACK, radioactive agents, nitrate, HA 1077, calcium antagonists, angiotensin converting enzyme inhibitor, anti-inflammatory agents, steroidal agents, anti-mitotic agents, HMG CoA reductase inhibitors, colchicine, angiopeptin, cytoclasin B, and the like. Gene therapy agents might also be locally delivered to inhibit restenosis and/or promote angiogenesis, with suitable agents optionally being delivered via plasmid vectors or by viral vectors, and suitable agents including genes relating to VEGF, C-myb, FGF, transforming growth factor b. endothelial growth factor, protooncogenes such as C-myc, C-myg, CDC-2, PCNA, and the like. Local delivery of chemotherapeutic agents (which are used to treat malignancies) may be employed, such as adriamycin or Doxorubicin. Imaging Media such as contrast media, radioactively labeled agents, or the like may be locally delivered, as might other agents such as plasminogen additive as an adjunct to thrombolytic therapy, immunosuppressive agents, Corazo'n material, lytics, saline, or the like.

As seen in FIG. 23, positioning cage 110 and dottering device 151 may be advanced simultaneously or in alternating partial steps into and through the total occlusion. Alternatively, dottering device 151 may be advanced through the total occlusion while the expanded positioning cage remains at a fixed location. Regardless, some penetrator structure of the catheter system will preferably advance until a passage 153 is formed through the total occlusion. Once an opening, propagation plane, or pathway has been formed through the occlusion TO, a guide structure may be passed distally along passage 153 beyond the total occlusion.

In addition to use of cage 110 to protect the vessel wall W from harm by positioning of the penetrator, the cage may be advanced against the proximal portion of the occlusion TO as shown in FIG. 24A (in which cage 110 is shown in a partially expanded configuration 110a) and then expanded (to a more fully expanded configuration 110b) to assist in propagating a passage, plane, or pathway through the occlusion, as shown in FIG. 24B. In other words, expansion of cage 110 may open up or propagate a cleavage plane to facilitate passing a guidewire or dottering device 51 using a wedge effect. This wedge effect may, of course, be combined with axial cycling of dottering device 51, rotation and advancement of a cutter, occlusive material agent dissolution, and any of the other mechanisms described herein. Similarly, the various occlusion treatment methods and structures described herein will generally be compatible for use in combination.

Figure 25A:
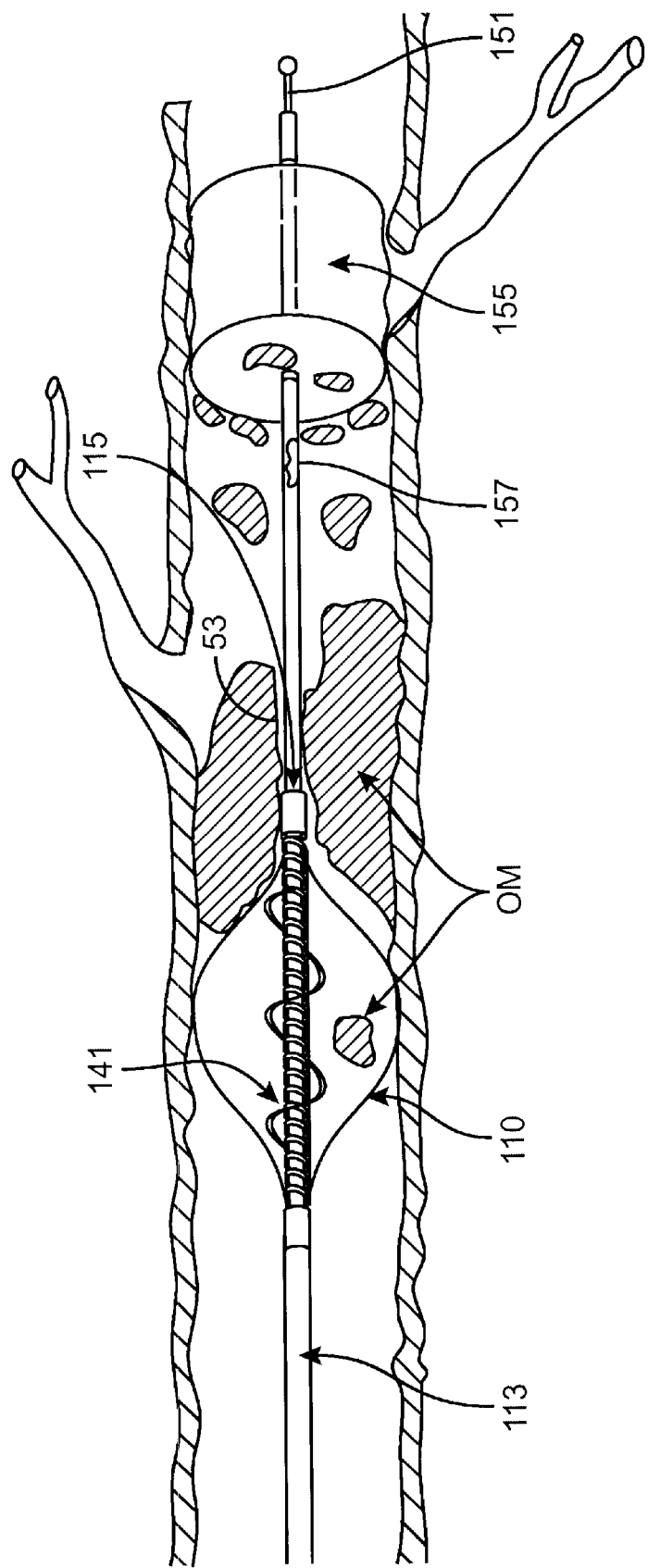
Figure 25B:
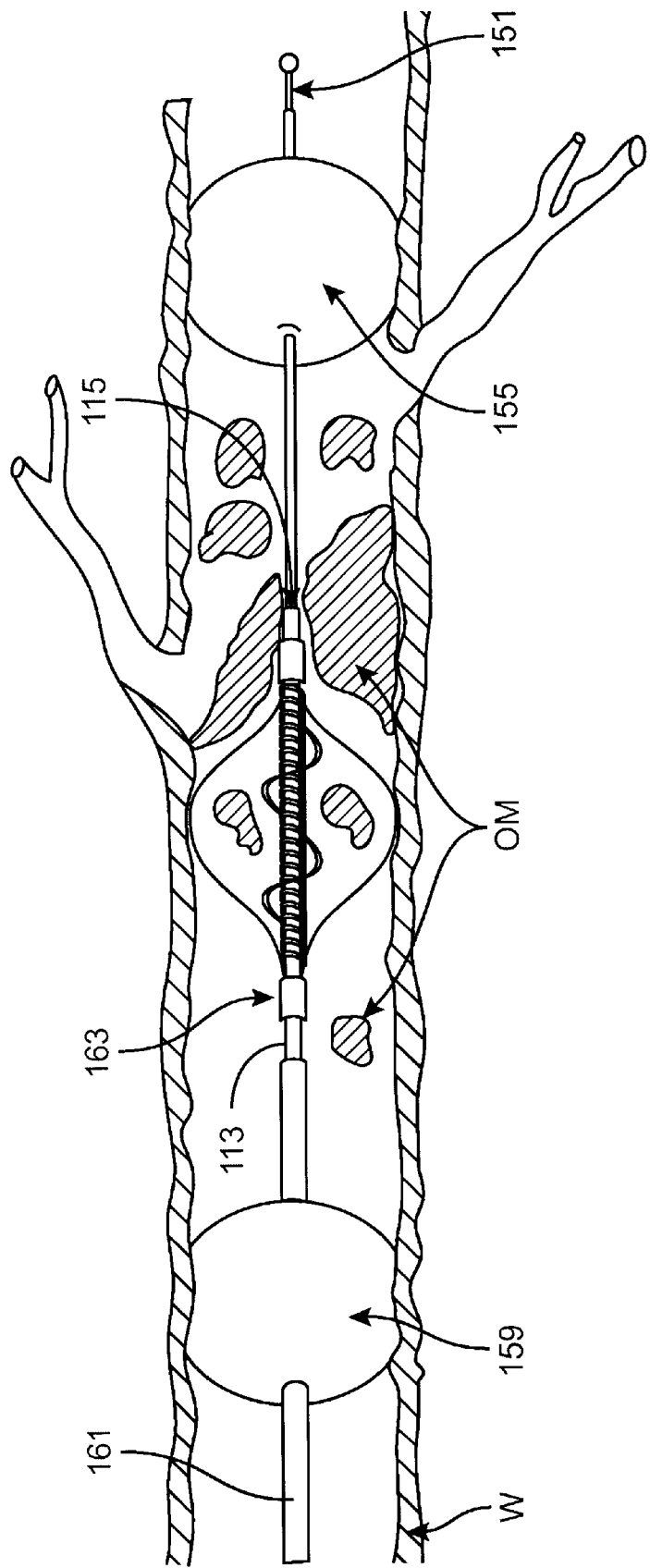

FIGS. 25A–25B illustrate further steps in treatment of the occlusion (TO) once a guidewire has been passed distally. As illustrated, a distal protection member 155 is inserted over the guidewire (or is attached to the guidewire itself) through passage 153 and expanded distally of the occlusion. Distal protection member 155 inhibits distal flow beyond the occlusion and can help decrease or prevent embolization of material downstream of the treatment site. Distal member 155 may comprise an annular balloon fixed on a catheter or guidewire, a radially expandable filter, or any of a wide variety of flow and/or embolization inhibiting intraluminal structures. Optionally, an intravascular ultrasound (IVUS) sensor 157 may be carried by at least one of the components of the catheter system, optionally in a component which will traverse the occlusion such as the guidewire or dottering device 151 (or other penetrator), a shaft axially coupled to distal protection member 155, or the like. Alternatively, IVUS capabilities may be incorporated in one or more of the other catheter system components, or may be provided by a dedicated structure that can be advanced through a lumen of the catheter system or independent thereof. Such IVUS capabilities may be useful for planning an occlusion therapy, for monitoring progress of the therapy, and/or for verifying the effectiveness of the therapy.

Once flow distal of the occlusive material OM is inhibited, treatment of the lesion can continue using any of a wide variety of modalities of treatment such as atherectomy, endarterectomy, infusion of occlusive material removal flow or active agents, and the like. Alternatively, as shown in FIG. 25B, a proximal occluding member 159 may also be inflated or expanded to isolate the treatment site. Proximal occluding member may again comprise a balloon or embolic filter carried on the outer surface of shaft 113 or on an outer sheath 161, with occlusion and fluid isolation allowing the infusion of various treatment modalities such as saline, contrast, pharmacologic agents such as tPA, ReoPro, IIB3A inhibitors and the like, or chemical ablation agents or acid solutions such as those listed above regarding FIGS. 22 and 23, and/or those described in PCT Application No. PCT/US99/15918 (Publication No. WO 00/03651). In the case of any acidic compounds, it is beneficial to fully contain the compounds infused within the treatment site, and to expeditiously remove and aspirate the dissolved material.

In FIGS. 25B and C, the treatment catheter 130, and specifically the mechanical pump (141 and 141') is used to remove some or all remaining occlusive material OM, including thrombus, plaque, fibrin, clot and the like, while still protecting the vessel wall. Fluid may optionally be circulated by, for example, infusion via lumen 115 while aspirating via a lumen 163 of shaft 113, the aspiration often being assisted by rotation of the Archimedes screw pump 141' within the aspiration lumen as described above. A vacuum source may be applied to the aspiration lumen via the proximal housing or only a proximal pump may be included, and some embodiments of the occlusion removal and access catheters described herein may not include an integral mechanical pump disposed in a distal lumen of the catheter system. The catheter is then removed and the vessel may then be further treated with a liner, stent, coated stent, stent-graft, or the like, as is taught by the prior art and is known to those skilled in the art.

Figure 26:
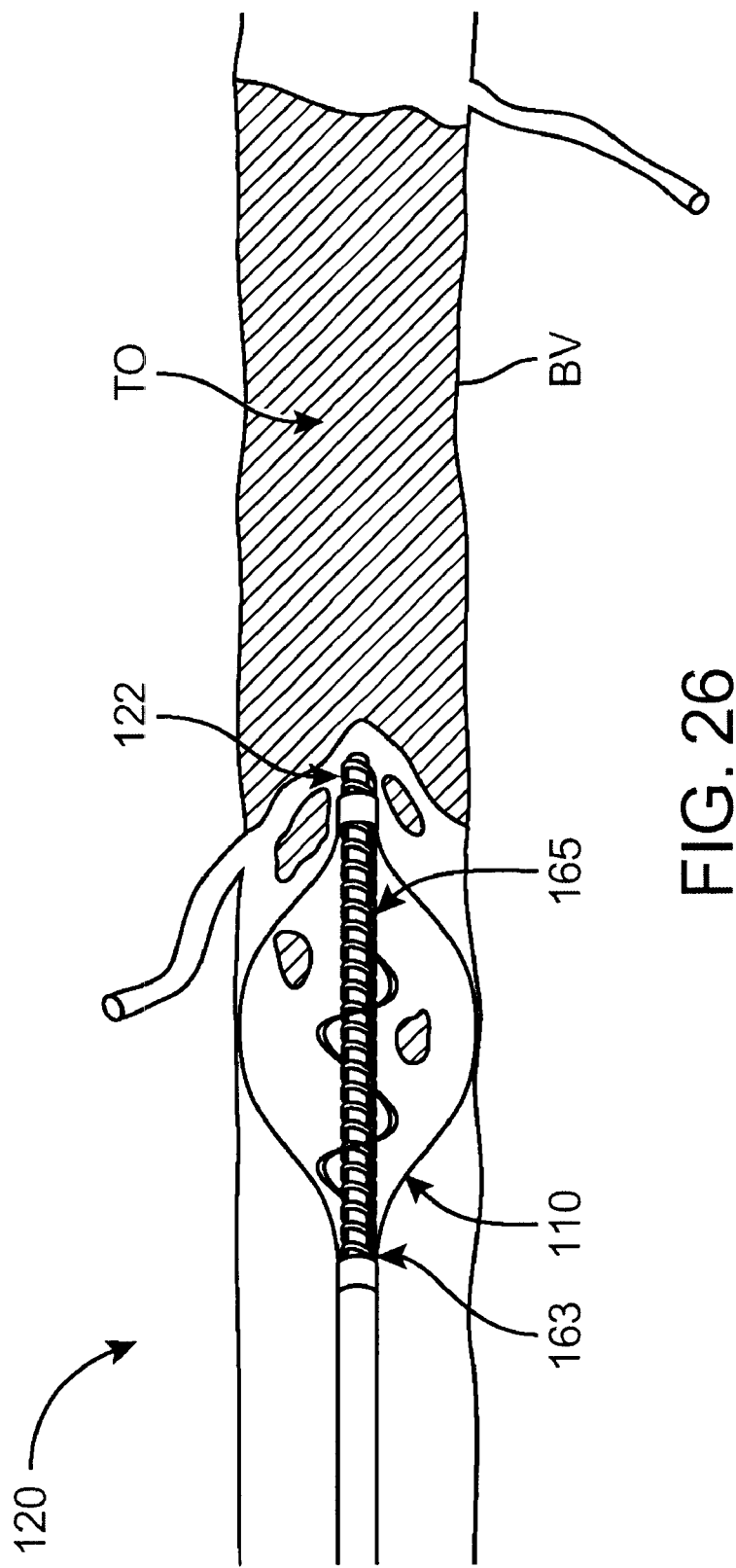
FIG. 26 illustrates an alternative embodiment of the present invention wherein a drive shaft is advanced to gain access through the total occlusion.

The use of the occlusive material removing catheter system embodiment of FIGS. 18C–E can be understood with reference to FIG. 26. Once again, a positioning cage 110 is located on the distal portion of a treatment catheter 120a. Treatment catheter 120a may include an axially moveable driveshaft 165, the cutters 122 may be axially affixed in a distally exposed configuration, or a distal cover may be removed in situ from cutters 122 of the morcellator. Regardless, the driveshaft 165 can be advanced into the occlusion TO while the driveshaft and (and the cutters carried thereon) rotate to create the desired pilot hole, propagation plane or passage for a guidewire or other guide device. Alternatively, the inner or outer cage may be translated distally and/or in tension to distally expose a morcellator that drills similarly into and/or through the total occlusion TO. Hence, a variety of related embodiments will be clear to those of skill in the art in light of the disclosure herein. For example, rather than a morcellator formed of helical cutters extending distally from within a lumen, the penetrator may comprise a blunt dissection tool distally extending from a fixed outer or rotating inner cage, a cutter in the form of a spinning burr or screw extending distally from a rotating inner cage, or the like.

It should be noted that any of the method steps or devices used in one method description may be interchanged with method steps of another description and still be in the scope of the present invention. For example, the isolation balloon or distal protection device may be used in conjunction with the positioning cage catheter 120, and well as through and in conjunction with treatment catheter 130. Furthermore, the terms pilot hole and propagation plane are used to refer to any path that is created through a occlusion (TO), either through the center of the vessel lumen, or to one side or the other around the circumference of the vessel lumen.

While the exemplary embodiments have been described in some detail, by way of example and for clarity of understanding, a variety of adaptations, changes, and modifications will be obvious to those of skill in the art. Hence, the scope of the present invention is limited solely by the appended claims.

What is claimed is:

1. A thrombectomy catheter comprising:

a flexible tubular body having a proximal end and a distal end;

an outer shearing member attached near the distal end, the outer member having a perforate inner surface; and an inner shearing member rotatably disposed within the outer member, the inner member having a proximal portion, a distal portion, and a circumferential series of struts extending therebetween, the struts sliding along the inner surface of the outer shearing member for shearing of clot material when the inner shearing member rotates, wherein the struts are helically oriented and have a local pitch that increases toward the proximal and distal portions sufficiently to inhibit excessive separation between adjacent struts when the outer shearing member flexes axially, and wherein the struts have protrusions which inhibit sliding of clot material axially between cooperating edges of the inner and outer shearing members.

2. The thrombectomy catheter of claim 1, wherein the inner member rotates about an axis, and wherein the inner and outer shearing bodies are sufficiently flexible to deflect the axis laterally when the outer shearing member engages a surrounding vessel and the inner member rotates therein.

3. The thrombectomy catheter of claim 1, wherein the struts uniformly coil distally toward a first circumferential orientation so that rotation of the inner shearing member toward the first circumferential orientation consistently urges sheared clot material proximally.

4. The thrombectomy catheter of claim 1, wherein the inner shearing member comprises tube material, the struts being separated by laser cut surfaces between adjacent tube material portions.

5. The thrombectomy catheter of claim 4, further comprising an expansible covering extending between adjacent struts of the outer basket to capture debris.

6. The thrombectomy catheter of claim 4, wherein the outer shearing member comprises outer tube material having a proximal outer portion, a distal outer portion and a circumferential series of outer struts extending helically therebetween, the struts being separated by laser cut outer surfaces between outer adjacent tube material portions.

7. The thrombectomy catheter of claim 1, wherein the struts are affixed together at the proximal portion and at the distal portion, and wherein the struts flex independently therebetween.

8. The thrombectomy catheter of claim 1, wherein at least one expansion actuator extends proximally from the shearing members so that the inner and outer shearing members can be radially expanded in situ.

9. The thrombectomy catheter of claim 8, wherein axial translation of an expansion actuator selectively radially expands the inner and outer shearing members concurrently.

10. The thrombectomy catheter of claim 1, further comprising a distally oriented clot penetrator adjacent the distal end.

11. The thrombectomy catheter of claim 10, wherein the occlusion penetrator comprises at least one end cutter that rotates with the inner shearing member and is exposed distally of the outer shearing member to advance the shearing members within a body lumen distally through clot material.

12. The thrombectomy catheter of claim 10, wherein the occlusion penetrator comprises a shaft extendable distally of the shearing members, the shaft axially cycleable through clot material without penetrating through a vessel wall.

13. The thrombectomy catheter of claim 1, further comprising an intravascular ultrasound sensor to measure of clot for removal.

14. A thrombectomy catheter comprising:

a flexible tubular body having a proximal end and a distal end;

a flexible drive shaft rotatably disposed within the tubular body;

an outer shearing member attached near the distal end of the tubular body, the outer member having a circumferential series of independent outer struts, the outer struts having inner surfaces; and an inner shearing member rotationally driven by the drive shaft within the outer member, the inner member having a proximal portion, a distal portion, and a circumferential series of independent inner struts, the inner struts having outer surfaces which slide across the inner surfaces of the outer struts so as to shear clot material when the inner shearing member rotates, at least one member of the group comprising the inner struts and the outer struts being helically oriented and having a local pitch that increases toward the proximal and distal portions sufficiently to inhibit excessive separation between adjacent struts when the outer shearing member flexes axially, wherein at least one member of the group comprising the inner struts and the outer struts have protrusions which inhibit sliding of clot material axially between cooperating edges of the inner and outer shearing members.

15. The thrombectomy catheter of claim 14, wherein the outer shearing member has an embolic debris capture coating.

16. The thrombectomy catheter of claim 14, wherein each of the inner and outer shearing members has a proximal portions and a distal portions, the struts of each shearing member affixed together at the proximal and distal portions and extending independently therebetween so that the shearing members flex axially primarily along the struts.

17. The thrombectomy catheter of claim 14, further comprising a proximal housing coupled to the tubular body, the housing having a motor drivingly engaging the drive shaft.

18. The thrombectomy catheter of claim 17, wherein the drive shaft engages the distal portion of the inner shearing member, wherein the drive shaft is axially translatable relative to the tubular body from adjacent the proximal housing, and wherein axial bearing surfaces of the outer and inner shearing members cooperate to effect concurrent radial expansion of the inner and outer shearing members when the drive shaft translates axially.

* * * * *